(12) United States Patent
Funakoshi et al.

(10) Patent No.: US 6,485,657 B1
(45) Date of Patent: Nov. 26, 2002

(54) GAMMA-RAY STABILIZER AND THERMOPLASTIC POLYMER COMPOUND INCLUDING THE SAID STABILIZER

(75) Inventors: Wataru Funakoshi, Yamaguchi (JP); Tetsuo Kanda, Yamaguchi (JP); Fumitaka Kondo, Yamaguchi (JP); Katsushi Sasaki, Yamaguchi (JP)

(73) Assignee: Teijin, Limited, Osaka (JP)

( * ) Notice: Subject to any disclaimer, the term of this patent is extended or adjusted under 35 U.S.C. 154(b) by 0 days.

(21) Appl. No.: 09/485,509

(22) PCT Filed: Jun. 10, 1999

(86) PCT No.: PCT/JP99/03111

§ 371 (c)(1),
(2), (4) Date: Feb. 11, 2000

(87) PCT Pub. No.: WO99/64506

PCT Pub. Date: Dec. 16, 1999

(30) Foreign Application Priority Data

Jun. 11, 1998 (JP) ............................................. 10-163571
Feb. 12, 1999 (JP) ............................................. 11-034509
Apr. 14, 1999 (JP) ............................................. 11-106414

(51) Int. Cl.$^7$ ............................. G21C 5/12; G21C 7/24
(52) U.S. Cl. ...................... 252/478; 524/115; 524/116; 524/120; 523/136
(58) Field of Search .......................... 252/478; 524/115, 524/116, 120; 210/321.71; 523/136

(56) References Cited

U.S. PATENT DOCUMENTS 4,774,275 A * 9/1988 Hisano et al. ............... 524/370
5,118,726 A * 6/1992 Mizutani .................... 523/136
5,510,237 A * 4/1996 Isogawa et al. ................. 435/2

FOREIGN PATENT DOCUMENTS

| JP | 60192759 | 10/1985 |
| JP | 62135556 | 6/1987 |
| JP | 2129261 | 5/1990 |
| JP | 2132147 | 5/1990 |
| JP | 5132552 | 5/1993 |
| JP | 5214233 | 5/1993 |
| JP | 5179127 | 7/1993 |
| JP | 384110 | 12/1995 |

* cited by examiner

Primary Examiner—Cephia D. Toomer
(74) Attorney, Agent, or Firm—Sughrue Mion, PLLC

(57) ABSTRACT

A new gamma-ray stabilizer comprising a combination of 100 parts by weight of a benzyl compound (A) having a specific chemical structure and 0.01 to 10 parts by weight of a pentaerythritol phosphorous ester (B) having a spirocyclic structure. Said stabilizer is preferably blended in such a manner that said (A) is contained in an amount of 0.01 to 10 parts by weight based on 100 parts by weight of a thermoplastic polymer (polycarbonate or the like), and said (B) is contained in an amount of 0.01 to 1 part by weight based on 100 parts by weight of said (A). When the thermoplastic polymer is subjected to gamma-ray irradiation, said stabilizer can efficiently protect the thermoplastic polymer from the deterioration of physical properties and yellowing; and on molding processing, the stabilizer-added polymer is suffered from little color tone deterioration and has excellent color tone, and at the same time, the polymer is scarcely suffered from molecular weight decrease on molding, and exhibits excellent thermal stability, moldability or the like. The thermoplastic polymer (especially polycarbonate) composition containing said stabilizer thus obtained is suitable for medical apparatus and medical material uses, especially a jacket case for an artificial dialyzer.

18 Claims, No Drawings

GAMMA-RAY STABILIZER AND THERMOPLASTIC POLYMER COMPOUND INCLUDING THE SAID STABILIZER

This application is a 371 of PCT/JP99/03111, filed Jun. 10, 1998.

TECHNICAL FIELD

The present invention relates to a new gamma-ray stabilizer and a thermoplastic polymer composition containing said stabilizer. More specifically the present invention is concerned with a new gamma-ray stabilizer having following advantages: the stabilizer can effectively protect a thermoplastic polymer (hereinafter referred to as "thermoplastic resin" in some cases or a molded product thereof against properties deterioration and yellowing when the thermoplastic polymer or the molded product undergoes gamma-ray irradiation; the incidences of decomposition reaction, foreign matter formation and color tone deterioration are few on molding processing of a thermoplastic resin which has been compounded with said gamma-ray stabilizer; and further the incidences of such various defects are also low in the molded product formed from the composition containing said gamma-ray stabilizer. The present invention is also concerned with a thermoplastic resin composition containing said gamma-ray stabilizer in a specific amount; and a molded product formed from said composition.

BACKGROUND ART

Medical apparatuses and supplies which are made of aromatic polyearbonate (hereinafter referred to simply as "polycarbonate") and many other thermoplastic resins are extensively used in the field of medical care. For example, because polycarbonate is a thermoplastic polymer having excellent characteristics in transparency, sanitation, dimensional stability, strength against impact, heat resistance and others, it is used for producing packaging materials for syringes and surgical instruments, artificial organs such as artificial lungs and kidneys, and various medical apparatuses such as surgical instruments and medical operation devices.

One of the most important required performances in such medical applications is the stability against various sterilization treatments. One of these sterilization methods is sterilization by gamma-ray irradiation. Compared with the conventional treatment by ethylene oxide or treatment by steam in an autoclave, this method provides less expensive dry sterilization at a lower temperature, and has come to find a wide application in recent years.

However, for example, when polycarbonate or its molded product is sterilized by gamma-ray irradiation, inherent transparence and clarity of the polycarbonate are extremely damaged, and the polycarbonate is yellowed and discolored in such a degree that the user feels uncomfortable; this problem is yet to be solved.

Many additives have been studied so far to prevent yellowing of the thermoplastic resin or molded products thereof due to gamma-ray irradiation For example, use of an alcohol such as aliphatic diol or polyol, a hindered phenol, or the like is disclosed in JP-A 60-192759 (JP-A means Japanese unexamined patent publication), while the use of a polyol such as polypropylene glycol is disclosed in JP-A 62-135556. Furthermore, the use of a specific polycarboxylic acid or acetal of benzaldehyde is mentioned in JP-A 2-132147. In addition, it is reported that an epoxy compound, a sulfur-containing compound, a boron compound and so forth have the effect of preventing yellowing due to gamma-ray irradiation.

However, these additives have problems as follows: a thermoplastic resin (e.g. polycarbonate) composition to which such a compound has been added does not have sufficient yellowing preventive effect; the properties of the resin composition are deteriorated when a sufficient amount of the compound is added for ensuring satisfactory effects; and the method of the addition to the thermoplastic resin is restricted due to the lack of sufficient heat resistance of the additive itself. Furthermore, there are other problems, that is, depending on the compound, when the gamma-ray irradiation is performed in a deoxygenated atmosphere, the same level of yellowing preventing effect as in the air cannot be achieved; or conversely, when gamma-ray irradiation is performed in the air, the yellowing preventing effect is small.

On the other hand, a method of using an organic halogen compound as a gamma-ray stabilizer is also known. For example, a method of using a bromine compound such as a tetrabromobisphenol A-type polycarbonate oligomer is disclosed in JP-A 2-129261, and a method of using a, nuclear bromine-substituted phthalic acid derivative is disclosed in JP-A 5-179127. Further, JP-A 5-214233 describes polyol compounds having halogen-substituted phenyl structures as a terminal group. These methods of using halogen compounds provide effective means for preventing yellowing whether gamma-ray irradiation is carried out in the air or in a deoxygenated atmosphere; however, these methods have disadvantages that environmental pollution problems arise when the resins containing the halogen compound or the products manufactured therefrom are discarded because of halogen atoms contained therein.

Furthermore, JP-A 5-132552 discloses the use of a polycarbonate which contains a p-hydroxybenzyl alcohol having hydrocarbyl group or hydrocarbyloxy group as an end cap agent. However, the production of this end capped polycarbonate resin requires a complicated manufacturing process, and the physical properties of the polymer itself are lowered by the use of a large amount of the end cap agent in order to enhance the yellowing prevention effect; these problems remain to be solved.

In addition, JP-A 8-225732 and European Patent Publication No. 384110 disclose compositions containing a benzyl compound as a gamma-ray stabilizer.

The composition containing a gamma-ray stabilizer of a prior art exhibits some effect in the prevention of yellowing of a thermoplastic resin (polyearbonate) caused by gamma-ray irradiation; however, when a molded product is produced by using such a composition, defects such as foaming, the occurrence of turbid spots or the generation of black foreign matters will appear in the molded products if molding is continued for a long period of time, for example, one to two days.

Especially, when an injection molding machine, which has been developed to improve the production efficiency of molded products, particularly a hot runner-type molding machine is used, the above-mentioned defects become more extreme.

PROBLEMS TO BE SOLVED BY THE INVENTION

The first object of the present invention is to provide a new gamma-ray stabilizer having the following advantages when added to a thermoplastic resin or a molded product thereof:

1) yellowing caused by gamma-ray irradiation during sterilization process is extremely little, 2) no lowering of physical properties nor generation of defects are observed on molding processing, 3) no deterioration of hue is detected even when the resin is held at a high temperature on molding processing, 4) the elution of the stabilizer is not observed at a steam treatment, 5) there are no problems when discarded, and so forth, and thereby capable of giving a thermoplastic resin composition useful for medical apparatuses, medical supplies and medical materials.

The second object of the present invention is to provide a highly stable thermoplastic polymer composition containing said new gamma-ray stabilizer.

The third object of the present invention is to provide a polycarbonate molded product prepared by injection molding from said composition.

The fourth object of the present invention is to provide medical materials, especially a molded product of a jacket case for an artificial dialyzer which is prepared by injection molding from the said highly stable thermoplastic polymer composition.

Still further objects of the present invention will become clear from the following descriptions.

MEANS FOR SOLVING THE PROBLEMS

The present inventors zealously pursued investigations to solve said problems and found that, when at least one kind of benzyl compound (A) having a specific chemical structure is compounded with at least one kind of pentaerythritol phosphorous ester (B) having a spirocyclic structure at a specific quantitative ratio, and the obtained mixture is blended to a thermoplastic resin, it is possible to effectively provide a thermoplastic resin composition and a molded product thereof having high stability against gamma-ray irradiation for sterilization, and free from the deterioration of hue and little suffered from the generation of defects on molding processing owing to the synergistic effect of the combination of said components (A) and (B); and we have completed the present invention.

That is, the first of the present inventions is, a new gamma-ray stabilizer characterized in that the stabilizer comprises substantially a benzyl compound (A) selected from the group consisting of the compounds expressed by the following general formulae (1), (2)and (3)

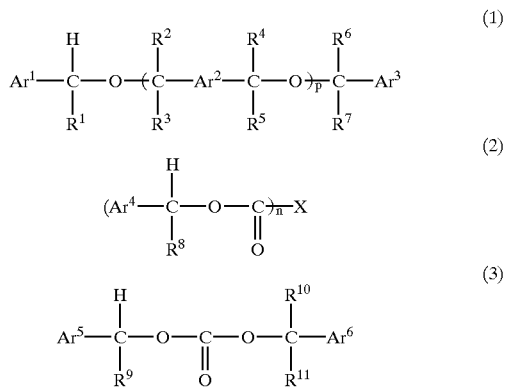

[wherein, $R^1$ to $R^{11}$ are each independently selected from the group consisting of a hydrogen atom, alkyl groups having 1 to 5 carbon atoms, cycloalkyl groups having 5 to 6 carbon atoms and aryl groups having 6 to 10 carbon atoms; $Ar^1$, $Ar^3$, $Ar^4$, $Ar^5$ and $Ar^6$ are each independently, may have one or more substituents, monovalent aromatic groups having 6 to 20 carbon atoms; $Ar^2$ is, may have one or more substituents,,a divalent aromatic group having 6 to 20 carbon atoms; p is 0 or 1; X is a direct bonding or a n-valent organic group having 1 to 20 carbon atoms, which may have one or more substituents; n is one of the integers 1 through 5], and a pentaerythritol phosphorous ester (B) having a spirocyclic structure; and the ratio of both the compounds is in the range of 0.01 to 10 parts by weight of said phosphorous ester (B) based on 100 parts by weight of said benzyl compound (A).

The second of the present inventions is a new resin composition having an excellent resistance to gamma-ray irradiation and characterized in that 100 parts by weight of a thermoplastic polymer, polycarbonate in particular, is compounded with 0.01 to 10 parts by weight of said benzyl compound (A) and said phosphorous ester (B), and the mount of the phosphorous ester (B) is in the range of 0.01 to 1 part by weight based on 100 parts by weight of the component A.

The third of the present inventions is an injection molded product made of said polycarbonate resin composition and having little deterioration in color tone on molding processing.

The fourth of the present invention is a polycarbonate composition having little lowering of physical properties and yellowing caused by gamma-ray irradiation and useful for a medical material, especially preferably a jacket case, for an artificial dialyzer, which is sterilized by gamma-ray irradiation.

EMBODIMENT FOR CARRYING OUT THE INVENTION

The gamma-ray stabilizer of the present invention substantially comprises a benzyl compound (A) having a specific chemical structure and a phosphorous ester (B) having a specific chemical structure. The following are specific descriptions for each component.

The benzyl compound (A) is selected from the group consisting of benzyl ether compounds (A)-1, benzyl ester compounds (A)-2 and benzyl carbonate compounds (A)-3, and it can be used singly or in combination of two or more kinds. Hereafter, each compound is described in detail.

(A) -1: Benzyl Ether Compound

The benzyl ether compound (A)-1 constituting: the gamma-ray stabilizer of the present invention is expressed by the following general formula (1):

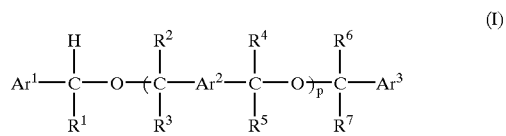

(wherein $R^1$ to $R^7$ are each independently selected from the group consisting of a hydrogen atom, alkyl groups having 1 to 5 carbon atoms, cycloalkyl groups having 5 to 6 carbon atoms and aryl groups having 6 to 10 carbon atoms; $Ar^1$ and $Ar^3$ are, each independently and may have one or more substituents, monovalent aromatic group having 6 to 20 carbon atoms; $Ar^2$ is, may have one or more substituents, a divalent aromatic group having 6 to 20 carbon atoms; p is 0 or 1)..

Examples of the alkyl groups RI to $R^7$ include methyl, ethyl and butyl groups and the like. Examples of the cycloalkyl groups include cyclopentyl and cyclohexyl groups. Examples of the aryl groups include phenyl group and the like.

In the benzyl ether compound of the present invention, all groups of $R^1$ to $R^7$ are preferably hydrogen atoms.

When said aromatic groups are not substituted, examples of $Ar^1$ and $Ar^3$ include phenyl and naphthyl groups, and examples of $Ar^2$ include phenylene and naphthylene groups. Further, when said aromatic group(s) are substituted, examples of the substituent(s) include alkyl groups such as methyl, ethyl, propyl, isopropyl, butyl, isobutyl, t-butyl, pentyl and hexyl groups; cycloalkyl groups such as cyclopentyl and cyclohexyl groups; alkoxy groups such as methoxy and ethoxy groups; acyloxy groups such as acetoxy and propionyloxy groups; aralkyl groups such as benzyl group; alkoxycarbonyl groups such as methoxycarbonyl and ethoxycarbonyl groups; aromatic groups such as phenyl, tolyl and naphthyl groups; acyl groups such as acetyl and benzoyl groups; cyano, nitro and carboxyl groups, halogen atoms such as chlorine and bromine atoms; hydroxymethyl group; and the like.

Furthermore, from the view point of gamma-ray stability, the molecular weight of the benzyl ether compound expressed by the above formula (1) is preferably not more than 1000. More preferably the molecular weight of said compound is not more than 500, especially preferably not more than 300. That is, the benzyl compound expressed by the following formula (1)-1:

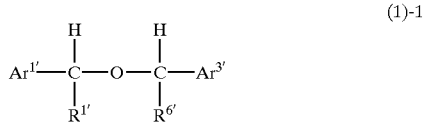

(1)-1

[wherein, $R^{1'}$ and $R^{6'}$ are each independently selected from the group consisting of a hydrogen atom, alkyl groups having 1 to 5 carbon atoms, cycloalkyl groups having 5 to 6 carbon atoms and aryl groups having 6 to 10 carbon atoms; $Ar^{1'}$ and $Ar^{3'}$ are each independently, may have one or more substituents, monovalent aromatic groups having, 6 to 20 carbon atoms] corresponding formula (1) where p=0 is preferred.

Specific examples of the above formula (1) include the following compounds.

In the case of p=0, those are dibenzyl ether, di(naphthylmethyl) ether, benzyl (naphthylmethyl) ether, benzyl (α-methylbenzyl) ether, benzyl (o-methylbenzyl) ether, benzyl (m-methylbenzyl) ether, benzyl p-methylbenzyl) ether, benzyl (o-methoxybenzyl) ether, benzyl (m-methoxybenzyl) ether, benzyl .-methoxybenzyl) ether, benzyl (o-acetoxybenzyl) ether, benzyl (m-acetoxybenzyl) ether, benzyl (p-acetoxybenzyl) ether, benzyl (o-benzylbenzyl) ether, benzyl (m-benzylbenzyl) ether, benzyl (p-benzylbenzyl) ether, benzyl (o-methoxycarbonylbenzyl) ether, benzyl(m-methoxycarbonylbenzyl) ether, benzyl (p-methoxycarbonylbenzyl) ether, benzyl (o-phenylbenzyl) ether, benzyl (m-phenylbenzyl) ether, benzyl (p-phenylbenzyl) ether, benzyl (o-acetylbenzyl) ether, benzyl (m-acetylbenzyl) ether, benzyl (p-acetylbenzyl) ether, benzyl (o-cyanobenzyl) ether, benzyl (m-cyanobenzyl) ether, benzyl (-cyanobenzyl) ether, benzyl (o-nitrobenzyl) ether, benzyl (m-nitrobenzyl) ether, benzyl (c-nitrobenzyl) ether, benzyl (o-bromobenzyl) ether, benzyl (p-bromobenzyl) ether, benzyl (m-bromobenzyl) ether, bis (o-methoxybenzyl) ether, bis(m-methoxybenzyl) ether, bis (p-methoxybenzyl) ether, bis(o-methylbenzyl) ether, bis(m-methylbenzyl) ether, bis(p-methylbenzyl) ether, bis(o-acetoxybenzyl) ether, bis(m-acetoxybenzyl) ether, bis(p-acetoxybenzyl) ether, bis(o-benzylbenzyl) ether, bis(m-benzylbenzyl) ether, bis(p-benzylbenzyl) ether, bis(o-methoxycarbonylbenzyl) ether, bis(m-methoxycarbonylbenzyl) ether, bis-(p-methoxycarbonylbenzyl) ether, bis(o-phenylbenzyl) ether, bis(m-phenylbenzyl) ether, bis(p-phenylbenzyl) ether, bis(o-acetylbenzyl) ether, bis(m-acetylbenzyl) ether, bis(p-acetylbenzyl) ether, bis(o-cyanobenzyl) ether, bis(m-cyanobenzyl) ether, bis(p-cyanobenzyl) ether, bis(o-nitrobenzyl) ether, bis(m-nitrobenzyl) ether, bis(p-nitrobenzyl) ether, bis(o-bromobenzyl) ether, bis(m-bromobenzyl) ether, bis(p-bromobenzyl) ether, bis(α-methylbenzyl) ether, bis(p-hydroxymethylbenzyl) ether, bis (m-hydroxymethylbenzyl) ether, and bis(o-hydroxymethylbenzyl) ether and the like.

Among them, bisbenzyl ether is preferred.

In the case of p=1, compounds as expressed in the following formulae (herein, Me expresses a methyl group) can be given as examples:

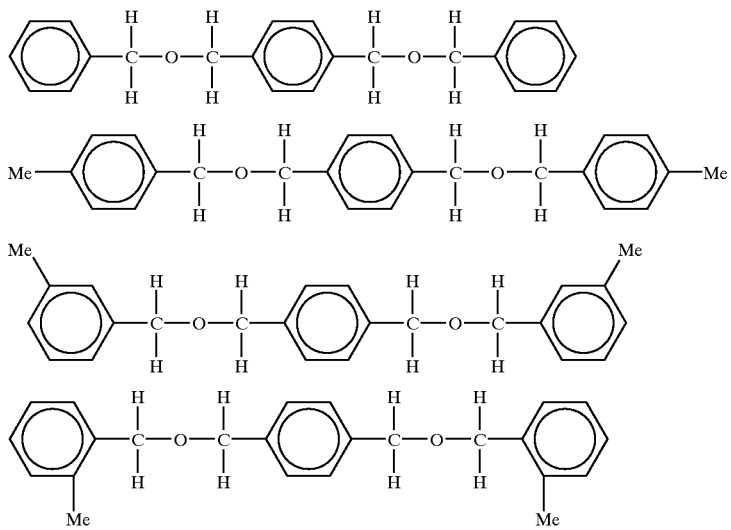

-continued
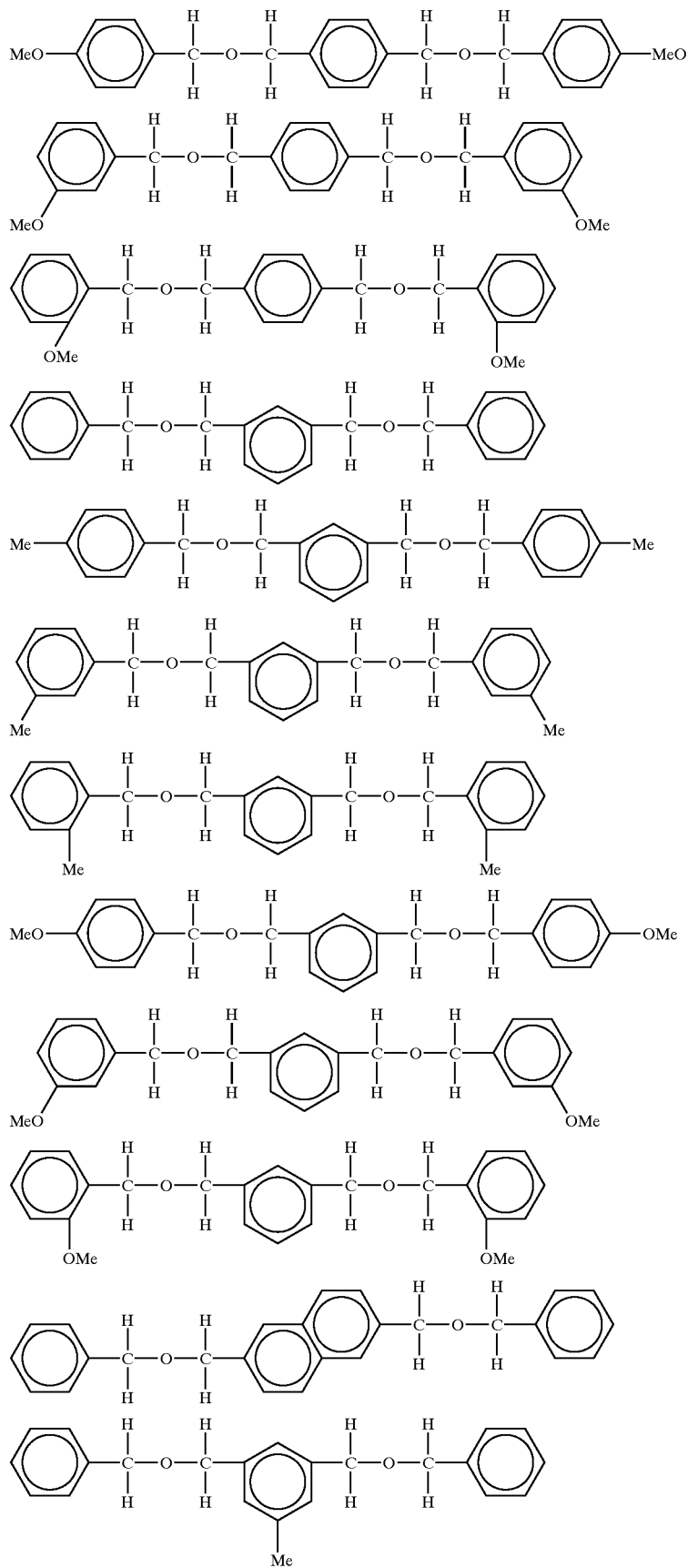

-continued

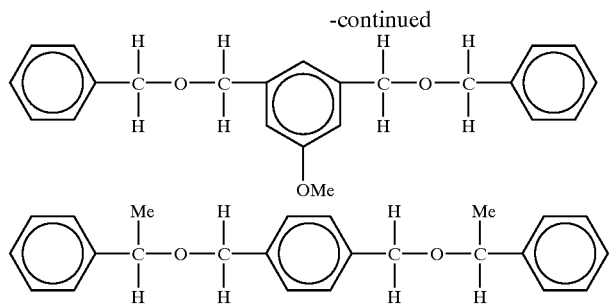

The above-mentioned benzyl ether compounds (A)-1 can be used singly or in combination of two or more kinds.

(A)-2: Benzyl Ester Compound

The benzyl ester compound (A)-2 constituting the gamma-ray stabilizer of the present invention is expressed by the following formula (2):

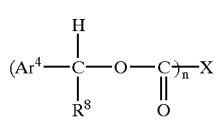

(2)

(in the formula (2), $R^8$ is selected from the group consisting of a hydrogen atom, alkyl groups having 1 to 20 carbon atoms, cycloalkyl groups having 5 to 20 carbon atoms and aryl groups having 6 to 20 carbon atoms; $Ar^4$ is, may have one or more substituents, an aryl group having 6 to 20 carbon atoms; X is a direct bond or a n-valent organic group having 1 to 20 carbon atoms, which may have one or more substituents; n is one of the integers 1 through 5).

In the formula (2), R8 is selected from the group consisting of a hydrogen atom, alkyl groups having 1 to 20 (preferably 1 to 5) carbon atoms; cycloalkyl groups having 5 to 20 (preferably 5 to 6) carbon atoms and aryl groups having 6 to 20 (preferably 6 to 10) carbon atoms. Here, examples of the alkyl groups include methyl, ethyl and butyl groups; examples of the cycloalkyl groups include cyclopentyl and cyclohexyl groups; and examples of the aryl groups include phenyl group. Especially preferred is. the case where $R^8$ is a hydrogen atom.

$Ar^4$ is , may have one or more substituents, aryl group having 6 to (preferably 6 to 10) carbon atoms. When said aryl group is not substituted, examples of $Ar^4$ include phenyl and naphthyl groups. When said aryl group has a substituent on the aromatic ring, examples of the substituent include alkyl groups such as methyl, ethyl, propyl, isopropyl, butyl, isobutyl, t-butyl, pentyl and hexyl groups; cycloalkyl groups such as cyclopentyl and cyclohexyl groups; alkoxy groups such as methoxy and ethoxy groups; acyloxy groups such as acetoxy and propionyloxy groups; aralkyl groups such as benzyl group; alkoxycarbonyl groups such as methoxycarbonyl and ethoxycarbonyl groups; aryl groups such as phenyl, tolyl and naphthyl groups; acyl groups such as acetyl and benzoyl groups; halogen atoms such as chlorine and bromine atoms; and cyano, nitro, carboxyl and hydroxymethyl groups.

Further, X in the formula (2) is a direct bond or, may have one or more substituents, n-valent organic group having 1 to 20 (preferably 1 to 10) carbon atoms. Examples of such an organic group include aliphatic residues having 1 to 20 (preferably 1 to 10) carbon atoms, and alicyclic or aromatic residues having 6 to 20 (preferably 6 to 10) carbon atoms.

The residues may have one or more substituents. Furthermore, n is one of the integers 1 through 5, and it is desirable to use a compound having n in this range as said benzyl ester compound.

Furthermore, from the view point of gamma-ray stability, the molecular weight of the benzyl ester compound expressed by the above formula (2) is preferably not more than 1000; the molecular weight of said compound is more preferably from 110 to 500.

Examples of the benzyl ester compound preferred in the present invention includes the following compounds:

Examples of the benzyl ester compound in which X is an organic group and n=1 in the above formula (2) include benzyl formate, o-methylbenzyl formate, p-methoxybenzyl formate, m-ethoxybenzyl formate, m-phenoxybenzyl formate, o-acetoxybenzyl formate, m-benzylbenzyl formate, o-methoxycarbonylbenzyl formate, o-benzoylbenzyl formate, p-cyanobenzyl formate, 2,6-dimethylbenzyl formate, p-methoxycarbonylbenzyl formate, methylnaphthyl acetate, α-butylbenzyl acetate, o-methoxycarbonylbenzyl acetate, p-ethoxycarbonylbenzyl acetate, m-butoxycarbonylbenzyl acetate, o-phenylbenzyl acetate, 2,4,6-trimethylbenzyl acetate, 4-t-butylbenzyl acetate, m-propionylbenzyl acetate, p-cyanobenzyl acetate, p-fluorobenzyl acetate, benzyl propionate, o-decylbenzyl propionate, m-cyclohexyloxybenzyl propionate, o-heptoxycarbonylbenzyl propionate, p-phenylbenzyl propionate, p-lauroylbenzyl propionate, a -methylbenzyl butyrate, benzyl butyrate, p-cyclohexylbenzyl butyrate, m-butylbenzyl butyrate, 2,4-dimethylbenzyl butyrate, o-ethoxybenzyl butyrate, m-methoxycarbonylbenzyl butyrate, 2,6-dichlorobenzyl butyrate, 2,4,6-trifluorobenzyl butyrate, m-methylbenzyl octoate, p-butylbenzyl octoate, m-cyclohexylbenzyl octoate, o-cyanobenzyl octanoate, p-benzoylbenzyl octanoate, o-cyclohexyloxybenzyl octanoate, 2,3-dichlorobenzyl octanoate, o-methylbenzyl decanoate, m-ethylbenzyl decanoate, 2,3-dimethylbenzyl decanoate, 2,4,6-trimethylbenzyl decanoate, o-phenylbenzyl decanoate, m-t-butylbenzyl decanoate, 2, 4-di-t-butylbenzyl decanoate, m-butoxycarbonylbenzyl decanoate, p-acetylbenzyl decanoate, p-methoxycarbonylbenzyl decanoate, α-ethylbenzyl decanoate, benzyl dodecanoate, benzyl hexadecanoate, p-butylbenzyl hexadecanoate, benzyl cyclohexanecarboxylate, m-methylbenzyl cyclohexanecarboxylate, 2,3-dimethylbenzyl cyclohexanecarboxylate, o-butoxybenzyl methylcyclohexanecarboxylate, benzyl cyclopentanecarboxylate, p-methoxycarbonylbenzyl cyclopentanecarboxylate, benzyl benzoate, benzyl m-methylbenzoate, p-ethylbenzyl p-ethylbenzoate, o-methoxybenzyl benzoate, p-acetoxybenzyl benzoate, m-methoxycarbonylbenzyl benzoate, p-butoxycarbonylbenzyl benzoate, m-benzylbenzyl benzoate, o-benzoylbenzyl 3-butylbenzoate, 2,4- dichlorobenzyl benzoate, benzyl 1-naphthoate, o-methylbenzyl 2-naphthoate, 2,4-dimethylbenzyl 1-naphthoate, and p-ethoxycarbonylbenzyl 2-naphthoate.

(ii) Examples of the benzyl ester compound in which X is a direct bond or an organic group, and n=2 in the above formula (2) include dibenzyl oxalate, bis(o-methylbenzyl) oxalate, bis(m-ethylbenzyl) oxalate, bis(p-butylbenzyl) oxalate, bis(α-ethylbenzyl) oxalate, bis(2,4-diacetylbenzyl) oxalate, bis(2,4,6-trimethoxybenzyl) oxalate, dibenzyl succinate, bis(o-methoxybenzyl) succinate, bis(m-phenoxybenzyl) succinate, bis(o-methoxycarbonylbenzyl) succinate, bis(p-phenoxycarbonylbenzyl) succinate, bis(m-acetylbenzyl) succinate, dibenzyl adip ate, bis(o-methylbenzyl) adipate, bis(m-ethylbenzyl) adipate, bis(2,4-dimethylbenzyl) adipate, bis(2,4,6-trimethylbenzyl) adipate, bis(p-cyanobenzyl) adipate, benzyl o-methylbenzyl adipate, p-chlorobenzyl p-methylbenzyl adipate, dibenzyl 1,4-cyclohexanedicarboxylate, bis(m-methylbenzyl) 1,3-cyclohexanedicarboxylate, bis(2,4-dimethylbenzyl) 1,4-cyclohexanedicarboxylate, bis(p-phenoxybenzyl) 1,2-cyclohexanedicarboxylate, bis(o-acetylbenzyl) 1,3-cyclohexanedicarboxylate, bis(o-cyanobenzyl) 1,4-cyclohexanedicarboxylate, dibenzyl terephthalate, bis(α-ethylbenzyl) terephthalate, bis(α-butoxybenzyl) terephthalate, bis(p-propylbenzyl) terephthalate, bis(2,6-dimethylbenzyl) terephthalate, bis(m-butoxybenzyl) terephthalate, bis(p-propionyloxybenzyl) terephthalate, bis (o-benzylbenzyl) terephthalate, bis(naphthylbenzyl) terephthalate, bis(p-lactoylbenzyl) terephthalate, bis(2,4-dicyanobenzyl) terephthalate, bis(2,4-difluorobenzyl) terephthalate, bis(α-ethylbenzyl) isophthalate, bis(p-t-butylbenzyl) isophthalate, bis(2,4,6-triethylbenzyl) isophthalate, bis(o-pentyloxybenzyl) isophthalate, bis(m-benzoyloxybenzyl) isophthalate, bis(m-caproylbenzyl) isophthalate, bis(α-ethoxybenzyl) phthalate, bis(m-hexylbenzyl) phthalate, bis(2,4-di-t-butyl-6-methylbenzyl) phthalate, bis(2,4-dimethoxybenzyl) phthalate, bis(m-acetoxybenzyl) phthalate, bis(2,4-dimethoxycarbonylbenzyl) phthalate, bis(m-palmitoylbenzyl) phthalate, dibenzyl 2,6-naphthalenedicarboxylate and dibenzyl 1,4-naphthalenedicarboxylate.

(iii) Examples of the benzyl ester compound in which X is an organic group and n is 3 or more in the above formula (2) include tribenzyl trimellitate, tris(o-methylbenzyl) trimellitate, tris(2,4-dimethylbenzyl) trimellitate, tris(o-ethoxybenzyl) trimellitate, tris(m-acetoxybenzyl) trimellitate, tris(o-methoxycarbonylbenzyl) trimellitate, tris (2,4-diacetylbenzyl) trimellitate, tetrabenzyl pyromellitate, tetrakis(o-ethylbenzyl) pyromellitate, tetrakis(2,6-dimethylbenzyl) pyromellitate, tetrakis(2,4-butoxybenzyl) pyromellitate, tetrabenzyl butane-tetracarboxylate, and tetrakis(p-methylbenzyl) butanetetracarboxylate.

The above-mentioned benzyl ester compounds (A)-2 can be used singly or in combination of two or more kinds.

Among these compounds (A)-2, the following are preferably used in the present invention: benzyl formate, o-methylbenzyl formate, benzyl acetate, 2,4,6-7trimethylbenzyl acetate, benzyl propionate, α-methylbenzyl butyrate, benzyl butyrate, m-methylbenzyl octoate, 2,3-dimethylbenzyl decanoate, benzyl dodecanoate, benzyl hexadecanoate, benzyl cyclohexanecarboxylate, 2,3-dimethylbenzyl cyclohexanecarboxylate, benzyl benzoate, p-acetoxybenzyl benzoate, dibenzyl oxalate, bis(p-butylbenzyl) oxalate, bis(α-ethylbenzyl) oxalate, dibenzyl succinate, bis(o-methoxybenzyl) succinate, bis(m-ethylbenzyl) adipate, bis(2,4,6-trimethylbenzyl) adipate, dibenzyl 1,4-cyclohexanedicarboxylate, bis(2,4-dimethylbenzyl) 1,4-cyclohexanedicarboxylate, dibenzyl terephthalate, bis(α-ethylbenzyl) terephthalate, bis(α-ethylbenzyl) isophthalate, bis(m-hexylbenzyl) phthalate, tribenzyl trimellitate, tetrabenzyl pyromellitate and the like. Benzyl formate, 4-t-butylbenzyl acetate, bis(2,4-dimethylbenzyl) decanoate, dibenzyl terephthalate, bis(2,6-dimethylbenzyl) adipate, bis(2,4-dimethylbenzyl) 1,3-cyclohexanedicarboxylate and the like are preferred in particular.

(A)-3: Benzyl Carbonate Compounds

The benzyl carbonate compound (A)-3 constituting the gamma-ray stabilizer of the present invention is expressed by the following formula (3):

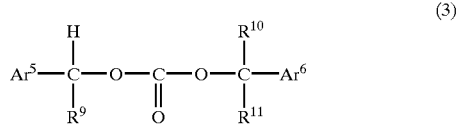

(wherein $R^9$, $R^{10}$ and $R^{11}$ are each independently selected from the group consisting of a hydrogen atom, alkyl groups having 1 to 20 carbon atoms, cycloalkyl groups having 5 to 20 carbon atoms and aryl groups having 6 to 20 carbon atoms; $Ar^5$ and $Ar^6$ are each independently, may have one. or more substituents, aryl groups having 6 to 20 carbon atoms).

In the formula (3), $R^9$, $R^{10}$ and $R^{11}$ are each independently selected from the group consisting of a hydrogen atom, alkyl groups having 1 to 20 (preferably 1 to 5) carbon atoms, cycloalkyl groups having 5 to 20 (preferably 5 to 6) carbon atoms and aryl groups having 6 to 20 (preferably 6 to 10) carbon atoms. Here, examples of the alkyl groups include methyl, ethyl and butyl groups; examples of the cycloalkyl groups include cyclopentyl and cyclohexvlgr;ups; and examples of the aryl groups include phenyl group. Especially preferred is the case where $R^9$, $R^{10}$ and $R^{11}$ are hydrogen atoms.

$Ar^5$ and $Ar^6$ are each independently, may have one or more substituents, aryl groups having 6 to 20 (preferably 6 to 10) carbon atoms. When said aryl group does not have substituent, examples of $Ar^5$ and $Ar^6$ include phenyl and naphthyl groups. When said aryl group has a substituent on its ring, examples of the substituent include alkyl groups such as methyl, ethyl, propyl, isopropyl, butyl, isobutyl, t-butyl, pentyl and hexyl groups; cycloalkyl groups such as cyclopentyl and cyclohexyl groups; alkoxy groups such as methoxy and ethoxy groups; acyloxy groups such as acetoxy and propionyloxy groups; aralkyl groups such as benzyl group; alkoxycarbonyl groups such as methoxycarbonyl and ethoxycarbonyl groups; aryl groups such as phenyl, tolyl and naphthyl groups; acyl groups such as acetyl and benzoyl groups; halogen atoms such as chlorine and bromine atoms; and cyano, nitro, carboxyl and hydroxymethyl groups.

Furthermore, from the view point of gamma-ray stability, the molecular weight of the benzyl carbonate compound expressed by the above formula (3) is preferably not more than 1000; the molecular weight of said compound is especially preferably of from 110 to 500.

Examples of the benzyl carbonate compound preferred in the present invention include dibenzyl carbonate, bis(α-ethylbenzyl) carbonate, bis(2,4-dimethylbenzyl) carbonate, bis(2,4,6-trimethylbenzyl) carbonate, bis(p-butoxybenzyl) carbonate, bis(2,3-dimethoxybenzyl) carbonate, bis(o-phenoxybenzyl) carbonate, bis(p-acetoxybenzyl) carbonate, bis(o-nonyloxycarbonylbenzyl) carbonate, bis(2,4- diphenylbenzyl) carbonate, bis(m-acetylbenzyl) carbonate, and bis(2, 4-difluorobenzyl) carbonate.

Among these benzyl carbonate compounds (A)-3, dibenzyl carbonate,. bis(α-ethylbenzyl) carbonate, bis(2,4-dimethylbenzyl) carbonate, bis(2,4,6-trimethylbenzyl) carbonate and the like are especially preferred in the present invention.

The above-mentioned benzyl carbonate compounds (A)-3 can be used singly or in combination of two or more kinds.

Examples of the benzyl alcohol giving the benzyl ester compound expressed by the above formula (2) or the benzyl carbonate compound expressed by the above formula (3) include the following alcohols:

1) benzyl alcohol and naphthylmethyl alcohol,
2) α-methylbenzyl alcohol, α-butylbenzyl alcohol, α-butoxybenzyl alcohol, α-phenoxybenzyl alcohol, α-cumylbenzyl alcohol and α-phenylbenzyl alcohol,
3) o-methylbenzyl alcohol, m-ethylbenzyl alcohol, p-propylbenzyl alcohol, o-n-butylbenzyl alcohol, p-t-butylbenzyl alcohol, m-hexylbenzyl alcohol, p-octylbenzyl alcohol and o-decylbenzyl alcohol,
4) 2,4-dimethylbenzyl alcohol, 2,6-dimethylbenzyl alcohol, 2,4,6-trimethylbenzyl alcohol, 2,4-di-t-butylbenzyl alcohol and 2,4-di-t-butyl-6-methylbenzyl alcohol,
5) o-methoxybenzyl alcohol, m-ethoxybenzyl alcohol, p-butoxybenzyl alcohol, o-pentyloxybenzyl alcohol, m-decyloxybenzyl alcohol, p-cyclohexyloxybenzyl alcohol, o-phenoxybenzyl alcohol and p-naphthyloxybenzyl alcohol,
6) o-acetoxybenzyl alcohol, m-propionyloxybenzyl alcohol, p-lactoyloxybenzyl alcohol, o-cetyloxybenzyl alcohol and o-benzoyloxybenzyl alcohol,
7) o-benzylbenzyl alcohol, m-benzylbenzyl alcohol and p-benzylbenzyl alcohol,
8) o-methoxycarbonylbenzyl alcohol, m-ethoxycarbonylbenzyl alcohol, p-butoxycarbonylbenzyl alcohol, o-pentyloxycarbonylbenzyl alcohol, m-heptoxycarbonylbenzyl alcohol and p-phenoxycarbonylbenzyl alcohol,
9) o-phenylbenzyl alcohol, m-phenylbenzyl alcohol and p-phenylbenzyl alcohol,
10) o-acetylbenzyl alcohol, m-propionylbenzyl alcohol, p-lactoylbenzyl alcohol, o-caproylbenzyl alcohol, m-lauroylbenzyl alcohol, p-benzoylbenzyl alcohol and m-naphthoylbenzyl alcohol,
11) o-cyanobenzyl alcohol, m-cyanobenzyl alcohol and p-cyanobenzyl alcohol,
12) o-nitrobenzyl alcohol, m-nitrobenzyl alcohol and p-nitrobenzyl alcohol,
13) o-bromobenzyl alcohol, m-bromobenzyl alcohol, p-bromobenzyl alcohol, o-chlorobenzyl alcohol, m-fluorobenzyl alcohol, and so forth.

(B) Phosphorous Ester Derived from Pentaerythritol and Having Spirocyclic Structure A pentaerythritol phosphorous ester (B) having a spirocyclic structure which constitutes the gamma-ray stabilizer of the present invention together with said benzyl compound (A) has one or more of the unit expressed by the following formula.

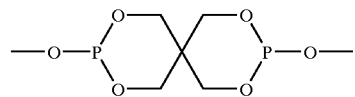

Specifically, it is a compound expressed by the following formula (4);

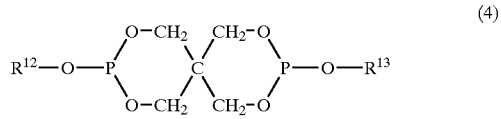

(wherein $R^{12}$ and $R^{13}$ are each independently a hydrogen atom, an alkyl group having 1 to 20 (preferably 1 to 10) carbon atoms, a cycloalkyl group having 3 to 20 (preferably 3 to 10) carbon atoms, an aryl group having 6 to 30 (preferably 6 to 20) carbon atoms, an aralkyl group having 6 to 30 (preferably 6 to 20) carbon atoms, an alkylaryl group having 6 to 30 (preferably 6 to 20) carbon atoms or a multivalent phenol residue; the aryl group, aralkyl group, alkylaryl group and multivalent phenol residue may have one or more substituents, each independently).

Use of a specific benzyl compound and a specific phosphorous ester in combination enables not only quality stabilization on molding processing, but also the enhancement of yellowing prevention effect by the specific benzyl compound during gamma-ray irradiation. As the phosphorous ester which suppresses the deterioration of physical properties on the molding of the resin composition and further enhances the gamma-ray resisting effect of the specific benzyl compound, the compounds expressed by the following two formulae are especially preferred among the compounds expressed by the above formula (4).

That is, it is preferable that the phosphorous ester compound is exexpressed by the following formula (4)-1.

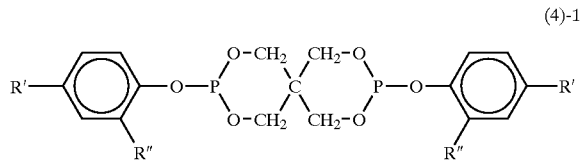

(wherein R' and R" are each independently, may have one or more substituents, tertiary alkyl groups having 4 to 20 carbon atoms). It is further preferable that R' and R" are each a t-butyl or t-amyl group.

In addition, it is preferable that the phosphorous ester compound is expressed by the following formula (4)-2.

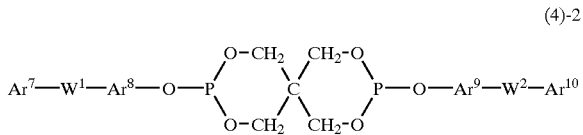

(wherein $Ar^7$ through $Ar^{10}$ are each independently, may have one or more substituents, aromatic groups having 6 to 30 carbon atoms; $W^1$ and $W^2$ are each independently an alkylidene group, an alkylene group, a cycloalkylidene group, a cycloalkylene group, a phenyl group-substituted alkylidene group, an oxygen atom, a sulfur atom, a sulfoxide group, a cycloalkylidene group, a cycloalkylene group, a phenyl group-substituted alkylidene group, an oxygen atom, a sulfur atom, a sulfoxide group, a sulfonyl group or a direct bond).

Specific examples of said phosphorous ester compounds (B) include the following compounds (No. 1 through No. 39). In the chemical formulae shown below, amyl denotes $C_5H_{11}$—, and Ph— shows a phenyl group. In some of the formulae, each —$CH_3$ of t-butyl group is omitted, and the t-butyl group is represented by X according to the practice in the art, and the representation of a spirocyclic carbon atom is simplified.

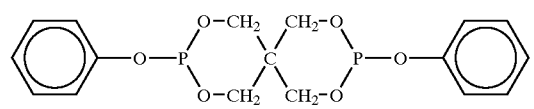

(No. 1)

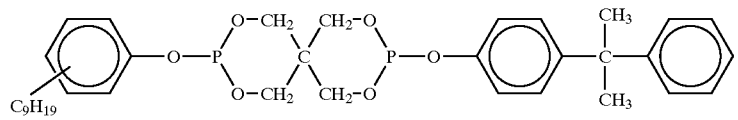

(No. 2)

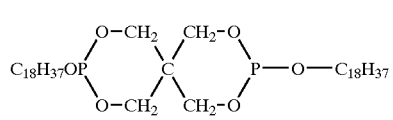

(No. 3)

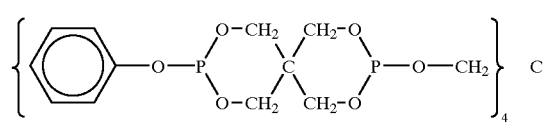

(No. 4)

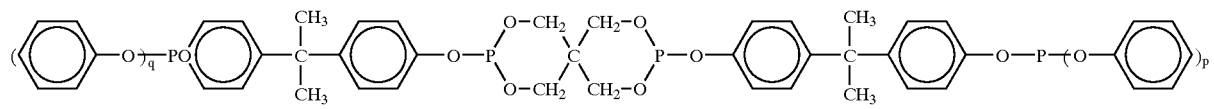

(No. 5)

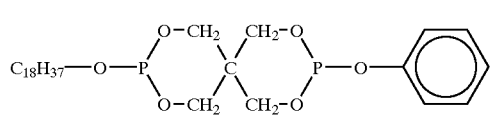

(No. 6)

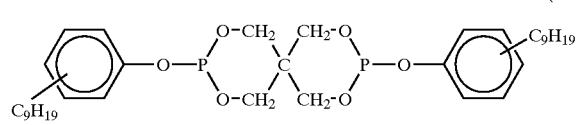

(No. 7)

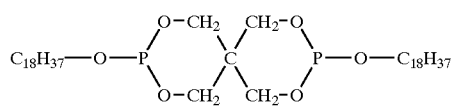

(No. 8)

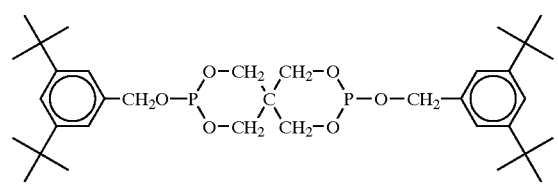

(No. 9)

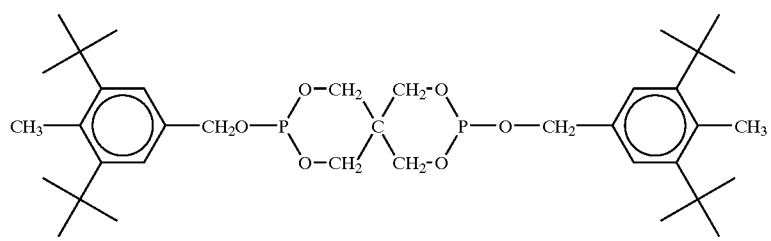

(No. 10)

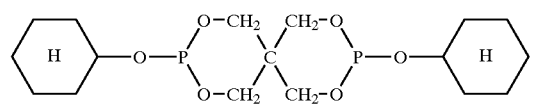

(No. 11)

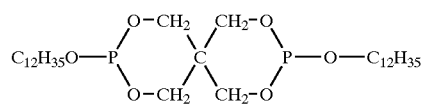

(No. 12)

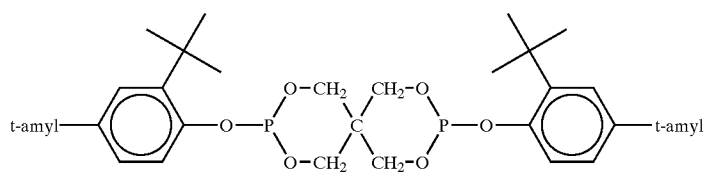

(No. 13)

-continued
(No. 14)
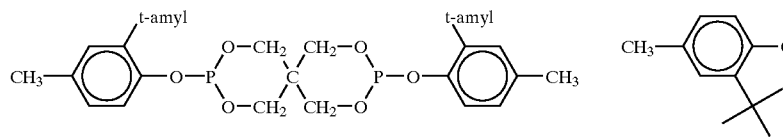
(No. 15)
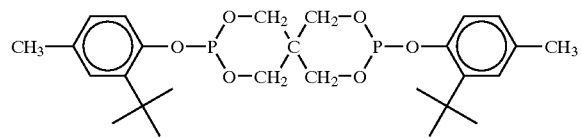
(No. 16)
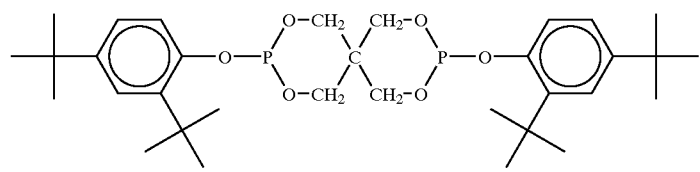
(No. 17)
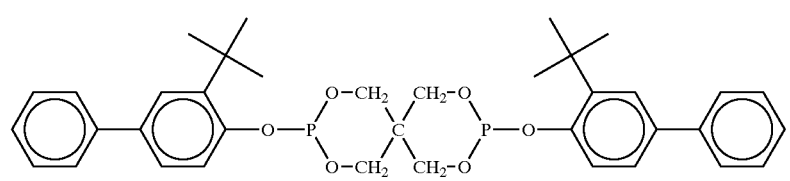
(No. 18)
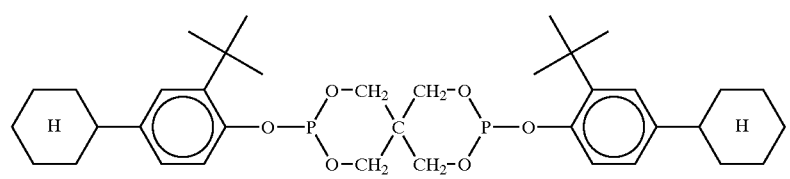
(No. 19)
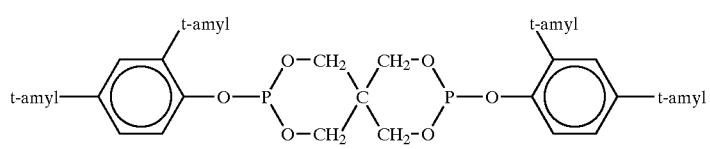
(No. 20)
(No. 21)
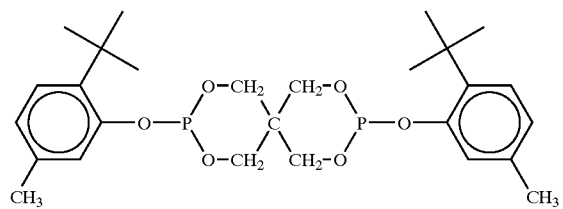
(No. 22)
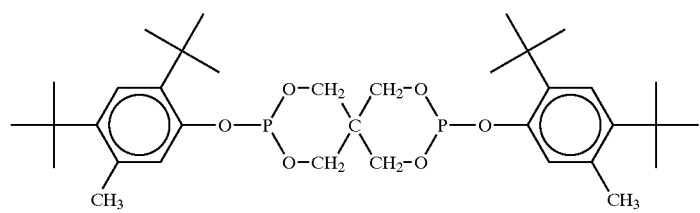
(No. 23)
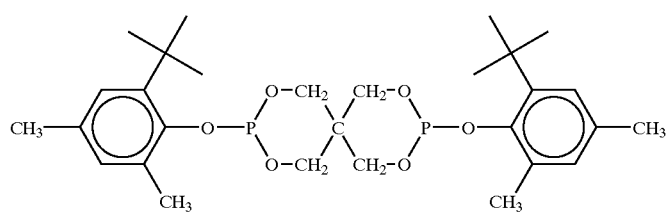

-continued
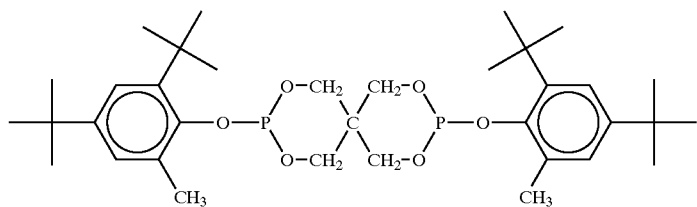
(No. 24)
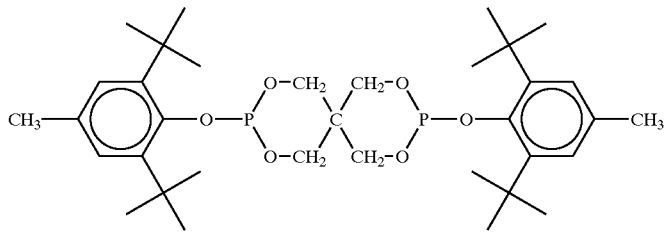
(No.25)
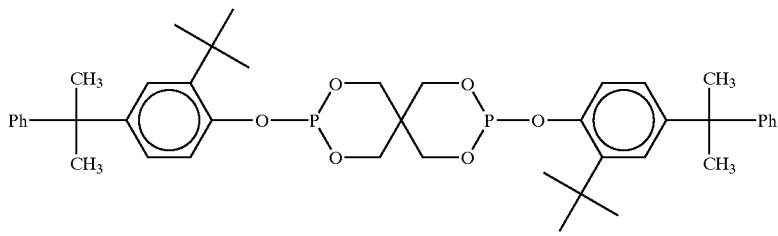
(No.26)
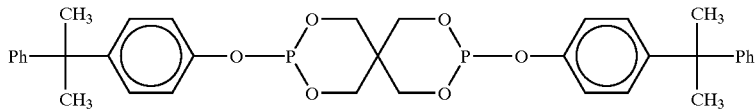
(No.27)
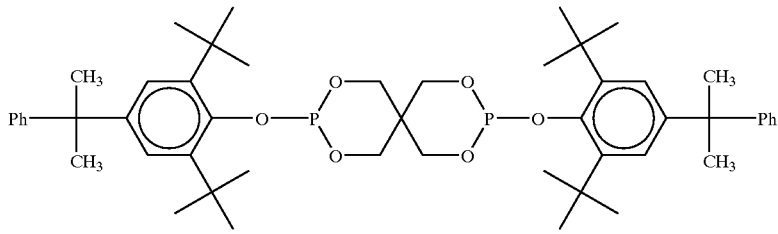
(No.28)
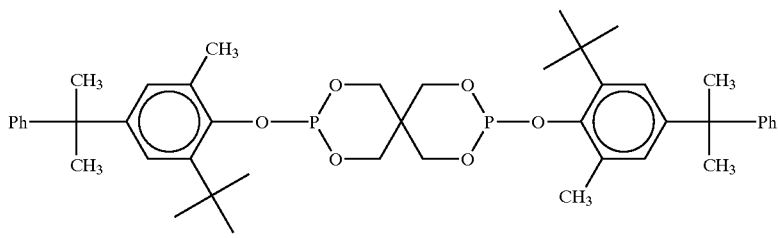
(No.29)
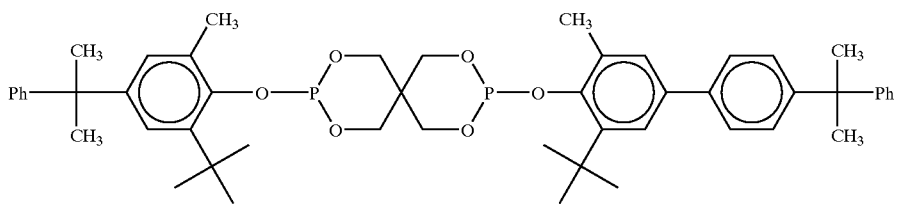
(No.30)

-continued
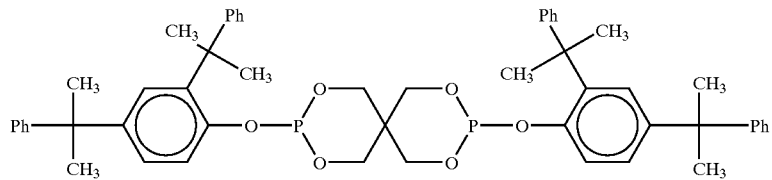
(No.31)
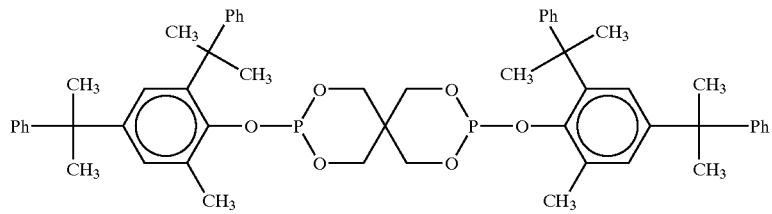
(No.32)
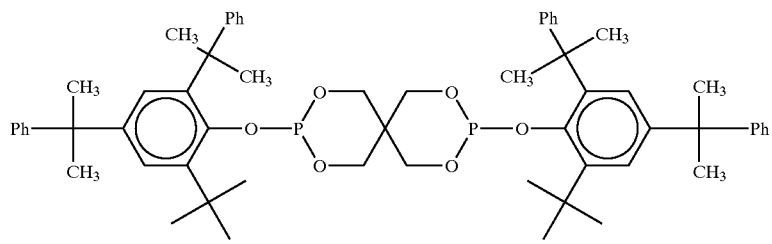
(No.33)
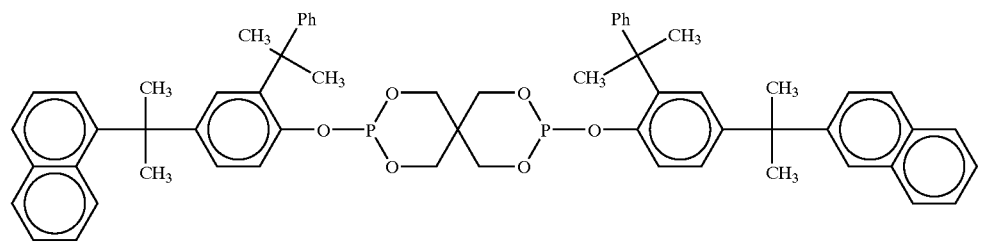
(No.34)
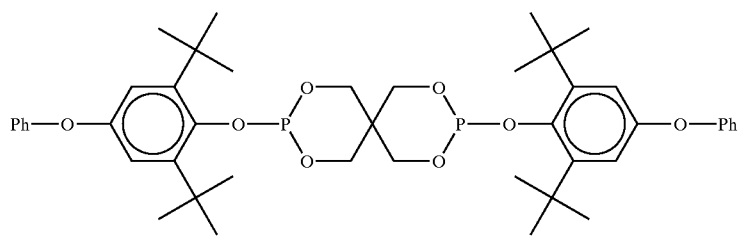
(No.35)
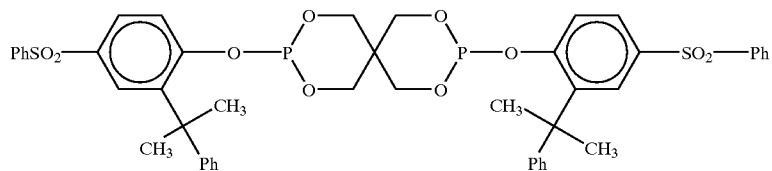
(No.36)
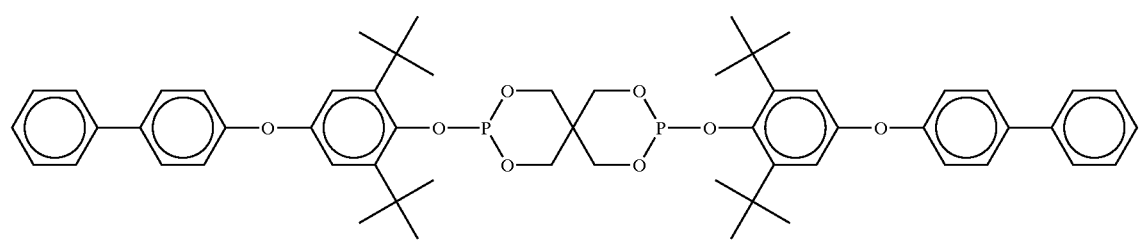
(No. 37)

(No. 38)

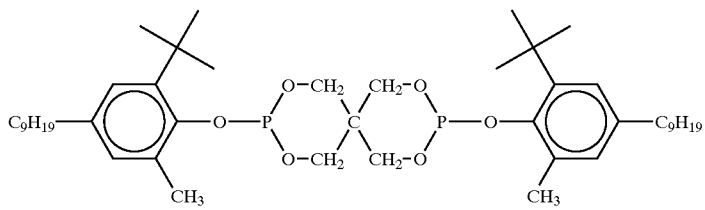

(No. 39)

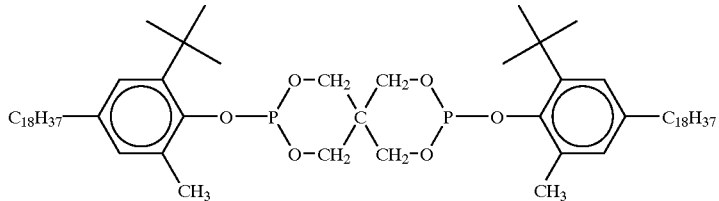

In addition, the phosphorous ester may be derived from a phosphorous acid having multiple spirocyclic structures, as shown below.

molding processing are prevented, and the color tone is not deteriorated even in the case of high temperature holding on molding processing.

(No. 40)

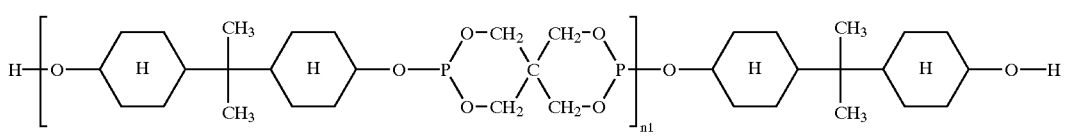

(No. 41)

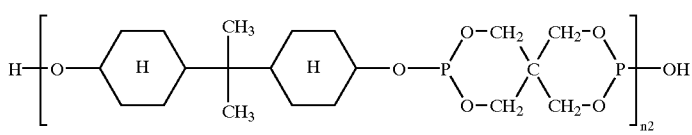

(No. 42)

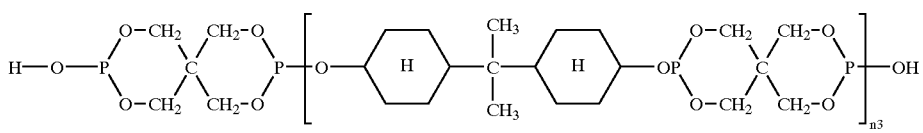

wherein $n_1$, $n_2$ and $n_3$ are each one of the integers of 2 through 10).

These phosphorous esters may be used singly or in combination of two or ore kinds.

Of said phosphorous esters (B), compounds. of Nos. 2, 3, 6, 13, 15, 16, 19, 23, 24, 26, 26, 30 and 31 are especially preferred in the present invention. Among them, compounds of Nos. 13, 16, 19, 24, 26, 30 and 31 are more preferred.

It is essential in the present invention that at least one kind of said benzyl compound (A) and at least one kind of pentaerythritol phosphorous ester (B) having a spirocyclic structure are combined and used in a specific ratio as constituents of the gamma-ray stabilizer used for thermoplastic resins represented by polycarbonate.

That is, the gamma-ray stabilizer of the present invention contains 0.01 to 10 parts by weight of said phosphorous ester (B) based on 100 parts by weight of said benzyl compound (A).

The use of said benzyl compound (A) and said pentaerythritol phosphorous ester (B) in combination at a specific ratio as the gamma-ray stabilizer obtains a polymer composition wherein the yellowing on the sterilization treatment with gamma-ray irradiation is extremely suppressed, the decay of the properties and the occurrence of defects on Particularly, the combination of a benzyl ether compound of the above formula (1), especially a benzyl ether compound of the above formula (1)-1 as the benzyl compound (A) and a phosphorous ester of the above formula (4), especially a phosphorous ester of the above formula (4)-i or (4)-2 as the phosphorous ester (B) is preferred in the point that the combination not only enables the stabilization of quality of the obtained resin composition on molding processing, but also enables the enhancement of the yellowing preventing effect for resin composition on gamma-ray irradiation as a gamma-ray stabilizer.

If the amount of said phosphorous ester (B) is less than 0.01 part based on 100 parts by weight of said benzyl compound (A), there is almost no effect of blending, that is, a synergistic effect for gamma-ray stabilization cannot be obtained. On the other hand, exceeding of 10 parts by weight of said phosphorous ester (B) is effective for gamma-ray stabilization, but since the phosphorous ester induces the decomposition of the benzyl compound, or lowers the stability of the polycarbonate against heat, water or the like and induces its decomposition, such a large amount of the phosphorous ester disadvantageously causes coloring of thermoplastic resin in a different sense.

In such a gamma-ray stabilizer, said benzyl compound (A) and said phosphorous ester (B), for example, can be separately added to thermoplastic resins such as polycarbonate; however, more preferably they are blended in advance in said ratio, and the blend is added before using, because this makes their synergistic effect exhibit sufficiently and enhances the improving effect on gamma-ray stability.

It has been known so far that various phosphorous esters are used as a coloring preventive agent or antioxidant on molding processing. However, it is completely unknown in the prior art that a combined use of a specific benzyl compound and a specific phosphorous ester as shown in the present invention not only enables quality stabilization on molding processing but also increases yellowing-preventing effect of the specific benzyl compound on gamma-ray irradiation; this finding is unique to the present invention.

The gamma-ray stabilizer of the present invention can be applied widely to all kinds of thermoplastic resins including styrene resins such as polystyrene and AS-resin, polyester resins such as polyethylene terephthalate, polybutylene naphthalate and polyethylene naphthalate, polycarbonate resins, and acrylic resins such as PMMA; however, when applied to polycarbonate among these thermoplastic resins, the effect thereof is exhibited in a remarkable and effective manner. Accordingly, the present invention will be explained using examples in which the gamma-ray stabilizer is applied to polyearbonates.

In the present invention, the polycarbonate is a thermoplastic polymer which consists substantially of a repeating unit represented by the following formula (5)

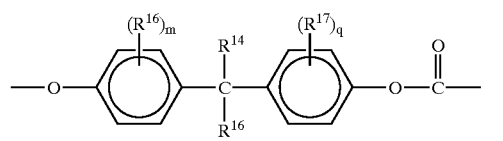

(5)

in the formula (5), $R^{14}$ and $R^{15}$ are each independently selected from the group consisting of a hydrogen atom, alkyl groups having 1 to 5 carbon atoms and cycloalkyl groups having 5 to 10 carbon atoms, and $R^{14}$ and $R^{15}$ may be bonded with each other; $R^{16}$ and $R^{17}$ are each independently a substituent selected from the group consisting of alkyl groups having 1 to 5 carbon atoms, halogen atoms and phenyl group; m and q are each independently 0, 1 or 2.)

Examples of $R^{14}$ and $R^{15}$ in the above-mentioned formula include methyl, ethyl, propyl, normal butyl, isobutyl, pentyl and cyclohexyl groups. A cycloalkane ring is formed when $R^{14}$ and $R^{15}$ are bonded with each other. Further, examples of $R^{16}$ and $R^{17}$ include methyl, ethyl, propyl, normal butyl, isobutyl, pentyl and phenyl groups, chlorine atom and bromine atom.

The polycarbonate represented by the above formula (5) can be a copolymer containing two or more of said repeating units, or can be a blended polymer. Further, some of the repeating units of the polymer may contain ester bonds.

Particularly preferred polycarbonate can be exemplified by the bisphenol A type polycarbonate where both $R^{14}$ and $R^{15}$ are methyl groups, and both m and q are 0. The viscosity averaged molecular weight of said polycarbonate is 15,000 to 40,000, or more preferably 20,000 to 35,000.

Typical production methods for such a polycarbonate are commonly an interfacial polymerization method (solution polymerization method) and a melt polymerization method (transesterification method).

In the interfacial polymerization method using phosgene, generally, a divalent phenol is dissolved into an aqueous solution of an acid binder, and the phenol is made to react with the phosgene in the presence of a solvent. An alkali metal hydroxide such as sodium hydroxide or potassium hydroxide is used as the acid binder, while a halogenated hydrocarbon such as methylene chloride or chlorobenzene is used as the solvent.

In the reaction, a end-capping agent is commonly used. The preferred examples of the end-capping agent are monovalent phenols like p-butylphenol and cumylphenol. The amount to be used is 0.01 to 10 mol %, preferably 0.03 to 8 mol % based on one mole of the divalent phenol. The appropriate reaction temperature is 0 to 40° C., preferably 20 to 30° C., and the appropriate reaction time is in the range about from ten minutes to ten hours. With the progress of the reaction, the pH value of the reaction system is preferably kept at 9 or more. A catalyst may be used to promote the reaction. Examples of the catalyst include tertiary amines such as triethylamine, quaternary ammonium compounds such as tetra-n-butylammonium bromide and quaternary phosphonium compounds such as tetra-n-butylphosphonium bromide.

On the other hand, in the melt polymerization method using a carbonic diester and a divalent phenol, the transesterification is carried out by distilling-off the formed phenol by heating under stirring in the atmosphere of an inert gas, preferably in the presence of a catalyst. The appropriate reaction temperature is usually in the range from 120 to 300° C. To promote the distilling-off of the formed phenol, the reaction is carried out in a weak vacuum of 200 to 100 mmHg at a reaction temperature of from 120 to 250° C. in the initial stage of the reaction; and in a high vacuum of 10 mmHg or less at a reaction temperature of from 200 to 300° C. in the later stage of the reaction. The reaction time is normally from one hour to ten hours; the reaction is continued until the desired degree of polymerization is reached. The following are used as the catalyst for the polymerization: hydroxides of alkali metals and alkaline earth metals, e.g. sodium hydroxide and potassium hydroxide; salts of boron or aluminum hydride; alkoxides; organic phenolates having monovalent, or polyvalent of divalent or higher valent; organic acid salts; carbonate; hydrocarbons; nitrates; nitrites; sulfites; cyanates; thiocyanates; borates; and organic tin, zinc, silicon, germanium, lead, antimony, manganese, titanium and zirconium compounds. Besides these compounds, a common transesterification catalyst or esterification catalyst such as a nitrogen-containing basic compound is used for the polymerization. The catalyst can be used singly, or in combination of two or more kinds. In the case of an alkali metal compound, the amount of the catalyst to be used is normally $10^{-8}$ to $10^{-5}$ chemical equivalent based on one mole of the divalent phenol used as the raw material; from the view point of polymer physical properties, preferably $10^{-7}$ to $5 \times 10^{-6}$ chemical equivalent, more preferably $10^{-7}$ to $2 \times 10^{-6}$ chemical equivalent. It is preferred to deactivate the catalyst after the polymerization by a sulfonic acid phosphonium salt, a sulfonic acid ester or the like, which has been disclosed in JP-A 8-59975, because this improves the stability of the polymer.

The gamma-ray stabilizer of the present invention exhibits excellent effects of the present invention by blending 0.01 to 10 parts by weight of a benzyl compound (A) selected from the group consisting of the compounds expressed by said formulae (1), (2) and (3) based on 100 parts by weight of a polycarbonate, and 0.01 to 10 parts by weight of a pentaerythritol phosphorous ester (B) having a spirocyclic structure expressed by said formula (4) based on 100 parts by weight of (A), as described above. It is especially preferable that the total compounding ratio of said gamma-ray stabilizer is 1 to 10 parts by weight based on 100 parts by weight of the polycarbonate.

If the compounding ratio based on the polycarbonate is smaller than said range, there is a small effect on the prevention of yellowing at the time of gamma-ray irradiation and on the prevention of the occurrence of cloudiness and the generation of black foreign matters in molded products. On the other hand, if the compounding ratio is greater than said range, physical properties of the polymer are deteriorated in some cases The use of a specific benzyl compound (A) and a specific phosphorous ester (B) in the combination at a compounding ratio in said range not only enables quality stabilization on molding processing but also enhances yellowing-preventing effect of the specific benzyl compound on gamma-ray irradiation.

Particularly, the combination of a benzyl ether compound of the above formula (1), especially a benzyl ether compound of the above formula (1)-1 as the benzyl compound (A) and a phosphorous ester of the above formula (4), especially a phosphorous ester of the above formula (4)-1 or (4)-2 as the phosphorous ester (B) is preferred in the point that the combination not only enables the quality stabilization of the obtained resin composition on molding processing, but also enhances the yellowing preventing effect of the specific benzyl compound on gamma-ray irradiation.

For adding the gamma-ray stabilizer, previously known methods can be used. The gamma-ray stabilizer can be added in an arbitrary step of polycarbonate production, or in an arbitrary step of molding processing, i e. before or during molding processing. For example, it can be mixed in the raw material before polycarbonate production or it can be added in an arbitrary step during the polycondensation process of the polycarbonate. Further, it can be added after the completion of polycondensation in a step where, for example, the monomer or oligomer of the polyearbonate, or the solvent used for the production of the polycarbonate is removed, the polycarbonate is not yet converted into chips, and it is in a molten or dissolved state.

For the gamma-ray stabilizer, said (A) and (B) can be added separately to the polymer, but they are preferably blended in advance and added at the same time in order to exhibit the effects of the present invention. It is especially preferred in the sense mentioned above that a gamma-ray stabilizer mixture is prepared by homogeneously mixing both the components, and the mixture is added to the polycarbonate.

Masterbatch technique can be used for adding said gamma-ray stabilizer. In this technique, said gamma-ray stabilizer of high concentration is added to a small amount of a polycarbonate, and the polycarbonate containing the gamma-ray stabilizer of high concentration is blended into a great amount of the polycarbonate containing no gamma-ray stabilizer at a specified ratio, and then the mixture is subjected to extrusion granulation.

The thermoplastic resin composition mixed with the gamma-ray stabilizer of the present invention allows further addition of a desired additive in accordance with a particular objective. For example, one or two or more kinds of the following can be added: a flame retardant such as a halogen compound, a phosphorus compound or a metal salt of sulfonic acid, a flame retardant assistant such as an antimony compound or: a zirconium compound, a drip-proof agent in catching fire such as polytetrafluoroethylene or a silicon compound, all of which can impart flame retardancy to the composition; an impact strength improving agent such as an elastomer; and an antioxidant, a thermal stabilizer, an ultraviolet-ray absorber, an antistatic agent, a plasticizer, a mold-releasing agent, a lubricant, a compatibihlzer and a foaming agent.

The thermoplastic resin composition containing the gamma-ray stabilizer of the present invention can be converted into a desired molded product according to a conventional molding method such as injection molding using a cold runner, injection molding using a hot runner or blow molding. The injection molded product made of the polycarbonate resin composition of the present invention exhibits very little deterioration of color tone while molding processing, and therefore it is possible to get efficiently an injection molded product having good color tone by using the polycarbonate resin composition of the present invention. Particularly, even in the case where the polymer is subjected to injection molding at a high temperature like in the injection molding using a hot liner, an excellently stable molded article free from deterioration attributable to defects such as foaming, the occurrence of turbid spots or the generation of black foreign matters can be obtained.

The present invention provides polycarbonate compositions having excellent gamma-ray stability. Specific examples of the molded articles for medical use, where these resin compositions are preferably applied, include an artificial dialyzer, an artificial lung, an anesthetic inhaler, a vein connector and accessories thereof, a blood centrifugal separation bowl, a surgical instrument, a medical operation device, and a container for intravenous injection solution or the like. Especially, the polycarbonate composition of the present invention is preferably used for a jacket case of an artificial dialyzer. Needles to say, they are useful in further applications.

Gamma-ray irradiation for sterilizing these molded articles for medical use is performed in an atmosphere of air, a deoxygenated gas or the like; however, the use of the gamma-ray stabilizer of the present invention suppresses the yellowing and discoloring of a thermoplastic polymer such as polycarbonate in any atmosphere.

Effects of the Invention

The gamma-ray stabilizer of the present invention does not cause the loss of various original characteristics of a thermoplastic resin when it is mixed to the thermoplastic resin, and further it can provide a thermoplastic resin composition which not only has little yellowing due to gamma-ray irradiation in any irradiation atmosphere, but also can produce molded articles having stable quality and having little defect of the occurrence of turbidness, cloudiness, black foreign matters and the like even in the case where it is molded at a high temperature. Furthermore, the stabilizer is excellent in stability, so that it does not elude from the molded article of said thermoplastic resin even on vapor treatment.

Especially, when mixed to polycarbonate, said stabilizer provides a polycarbonate resin composition having little yellowing due to gamma-ray irradiation without causing the loss of excellent characteristics inherent to the polycarbonate such as transparency, sanitation, dimensional stability, impact strength and thermal resistance. The obtained polycarbonate resin composition, when molded, produces molded products having stable quality and free from the occurrence of defects such as turbidness, cloudiness, black foreign matters and the like.

Accordingly, the composition containing this gamma-ray stabilizer is stable against sterilization by gamma-ray irradiation, and it is particularly preferred for medical application. The composition containing the gamma-ray stabilizer of the present invention is improved also in the impact on the environment when scrapped. and discarded.

EXAMPLES

The following provides detailed description of the present invention with reference to Examples and Comparative Examples; however, it should not be understood that the present invention is limited by the following examples.

Examples 1 through 24

To 500 parts by weight of a commercially available polycarbonate resin (registered trade name "Panlite" L1250 by Teijin Kasei Co., Ltd.) were added a benzyl compound (A) and a pentaerythritol phosphorous ester (B) shown in the following Table 1 and 2 in the amounts (parts by weight) shown in the Tables 1 and 2, respectively. They were molten and kneaded at a polymer temperature of 280° C. for an average residence time of 3 minutes by using a 30 mm-diameter twin-screw extruder having unidirectionally revolving screws (by Ikegai Iron Works) to obtain a polycarbonate resin composition containing the gamma-ray stabilizer.

After that, an injection molding machine (model M-50B by Meiki Seisakusho Co., Ltd.) was used to perform injection molding at a cylinder temperature of 280° C. and a mold temperature of 60° C. to produce a 2-mm thick disk-shaped molded product. The molded product was subjected to 25 KGy gamma-ray irradiation treatments in deoxygenated atmosphere and in air, respectively. A yellowness and a yellowing factor were measured within about two days, and the results are given in the Tables shown below. Further, the polymer composition was left in the cylinder for ten minutes during injection molding of said molded products, and successively the molding was restarted. The rates of cloudiness spots generated per 100 sheets of so-obtained molded product are also shown in the Tables.

Herein, the Yellow Index(YI) and yellowing factor ($\Delta$YI) of the molded product were measured by a transmission method according to the Japanese Industrial Standards K7103 using Model Z-300A of Nippon Denshoku Kogyo Co., Ltd. on 2-mm thick samples. The yellowing factor($\Delta$YI) was obtained by subtracting the value YI of the molded product before irradiation with 25 KGy gamma-ray from the value YI after the irradiation.

Said compounds (A) and (B) indicated by the numerals shown in the parentheses in Tables 1 and 2 have the following meanings:
Benzyl ether compound (A-1);
    (a1) Dibenzyl ether
    (a2) p-($\alpha$c, $\alpha$'- dibenzyloxy)xylylene
Benzyl ester compound (A-2);
    (a3) Benzyl formate
    (a4) 4-t-butylbenzyl acetate
    (a5) Bis(2,4-dimethylbenzyl) decanoate
    (a6) Dibenzyl terephthalate
    (a7) Bis(2,6-dimethylbenzyl) adipate
    (a8) Bis(2,4-dimethylbenzyl) 1,3-cyclohexanedicarboxylic acid ester
Benzyl carbonate compound (A-3);
    (a9) Dibenzyl carbonate
Phosphorous ester (B);

The numeral in a parenthesis in each Table shows the number of a phosphorus compound shown in the above specification or the number of a following phosphorous esters having no cyclic structure.
    (101) Triphenyl phosphite
    (102) Tristearyl phosphite
    (103) Trinonylphenyl phosphite
    (104) Diphenyl monodecyl phosphite
    (105) Tetrakis(diphenyl phosphite) pentaerythritol ester Comparative Examples 1 through 11

For the sake of comparison, the following cases were studied in experiments similar to the Examples: the case where the gamma-ray stabilizer was not added to said prescriptions; the case where the phosphorous ester was not added; the case where the benzyl compound was not added; and the case where the phosphorous ester having no cyclic structure such as triphenyl phosphite was used in stead of the pentaerythritol phosphorous ester. They were evaluated in the same manner, and the results are shown in Tables 1 and 2.

TABLE 1

| | | Benzyl ether compound (A-1) | | | | |
|---|---|---|---|---|---|---|
| | | (additive) amount | | characteristics of molded product | | yellowing factor $\Delta$YI after 25 KGY $\gamma$-ray irradiation |
| | | benzyl ether compound (A-1) | phosphorous ester compound (B) | Yellow Index (YI) | defects of cloudiness ratio, etc. | in air | in deoxidized gas |
| Example 1 | (a1) 2.5 | (1) 0.05 | 1.5 | 1 | 7.9 | 9.1 |
| Example 2 | (a1) 2.5 | (16) 0.08 | 1.5 | 1 | 7.5 | 9.0 |
| Example 3 | (a1) 5 | (3) 0.005 | 1.7 | 2 | 8 | 9.5 |
| Example 4 | (a1) 5 | (14) 0.01 | 1.7 | 1 | 7.9 | 9.3 |
| Example 5 | (a2) 5 | (24) 0.05 | 1.7 | 2 | 5.7 | 8.3 |
| Example 6 | (a2) 5 | (20) 0.05 | 1.8 | 2 | 5.8 | 8.8 |
| Example 7 | (a2) 5 | (16) 0.04 | 1.9 | 1 | 5.1 | 8.1 |
| Example 8 | (a2) 5 | (19) 0.05 | 1.8 | 1 | 5.3 | 8.9 |
| Example 9 | (a1) 2.5 | (32) 0.08 | 1.5 | 1 | 6.9 | 7.9 |
| Example 10 | (a1) 2.5 | (34) 0.08 | 1.5 | 1 | 6.8 | 7.9 |
| Example 11 | (a1) 5 | (33) 0.01 | 1.5 | 1 | 6.9 | 7.8 |
| Example 12 | (a2) 2.5 | (29) 0.01 | 1.6 | 1 | 7.2 | 8.4 |

TABLE 1-continued

| | (additive) amount | | characteristics of molded product | | yellowing factor ΔYI after 25 KGY γ-ray irradiation | |
|---|---|---|---|---|---|---|
| | benzyl ether compound (A-1) | phosphorous ester compound (B) | Yellow Index (YI) | defects of cloudiness ratio, etc. | in air | in deoxidized gas |
| Example 13 | (a2) 2.5 | (32) 0.01 | 1.5 | 1 | 6.9 | 7.8 |
| Comp. Ex. 1 | (a1) 2.5 | 0 | 2 | 12 | 8.8 | 15.6 |
| Comp. Ex. 2 | 0 | (1) 0.05 | 1.4 | 3 | 22.53 | 55.9 |
| Comp. Ex. 3 | (a1) 2.5 | (101) 0.05 | 2.1 | 12 | 8.8 | 16.1 |
| Comp. Ex. 4 | (a1) 2.5 | (102) 0.05 | 2.1 | 13 | 8.8 | 16.1 |
| Comp. Ex. 5 | (a2) 5 | 0 | 2.2 | 16 | 6.8 | 11.4 |
| Comp. Ex. 6 | (a2) 5 | (103) 0.05 | 2.1 | 17 | 6.9 | 12.2 |
| Comp. Ex. 7 | (a2) 5 | (104) 0.05 | 2.2 | 16 | 6.9 | 11.5 |
| Comp. Ex. 8 | (a2) 5 | (105) 0.05 | 2.2 | 15 | 7.1 | 12.4 |
| Comp. Ex. 9 | 0 | 0 | 1.4 | 2 | 22.53 | 55.79 |

In the above table, Comp. Ex. means Comparative Example.

TABLE 2

| | Benzyl ester/Benzyl carbonate compound (A-2, 3) | | | | | |
|---|---|---|---|---|---|---|
| | (additive) amount | | characteristics of molded product | | yellowing factor ΔYI after 25 KGY γ-ray irradiation | |
| | benzyl ester/carbonate compound (A-2,3) | phosphorous ester compound (B) | Yellow Index (YI) | defects of cloudiness ratio, etc. | in air | in deoxidized gas |
| Example 14 | (a3) 4.0 | (32) 0.04 | 1.5 | 1 | 5.7 | 8.4 |
| Example 15 | (a3) 4.0 | (23) 0.04 | 1.5 | 2 | 5.3 | 8.1 |
| Example 16 | (a3) 4.0 | (33) 0.04 | 1.7 | 1 | 5.3 | 8.4 |
| Example 17 | (a3) 4.0 | (16) 0.04 | 1.5 | 1 | 5.3 | 8.3 |
| Example 18 | (a3) 4.0 | (26) 0.04 | 1.5 | 1 | 5.5 | 8.5 |
| Example 19 | (a4) 3.0 | (32) 0.01 | 2 | 2 | 7.4 | 8.4 |
| Example 20 | (a5) 3.0 | (23) 0.07 | 2.2 | 1 | 7.7 | 8.6 |
| Example 21 | (a9) 3.0 | (33) 0.02 | 2.3 | 2 | 7.7 | 8.8 |
| Example 22 | (a6) 3.0 | (16) 0.015 | 2.3 | 2 | 7.5 | 8.6 |
| Example 23 | (a7) 3.0 | (16) 0.02 | 2.1 | 1 | 7.8 | 8.7 |
| Example 24 | (a8) 3.0 | (26) 0.03 | 2.3 | 2 | 7.8 | 8.8 |
| Comp. Ex. 10 | (a3) 4.0 | absent | 2.2 | 16 | 8.3 | 12.5 |
| Comp. Ex. 11 | (a3) 4.0 | (101) 0.04 | 2.3 | 12 | 7.9 | 15.4 |

In the above table, Comp. Ex. means Comparative Example.

Example 25 and Comparative Example 12

To 500 parts by weight of a commercially available polycarbonate resin (registered trade name "Panlite" L1250 by Teijin Kasei Co., Ltd.) were added a dibenzyl ether and a pentaerythritol phosphorous ester (phosphorus compound No. 16 shown in the above specification) or triphenyl phosphite in an amount (parts by weight) shown in Tables 3, respectively. They were molten and kneaded at a polymer temperature of 280° C. for an average residence time of 3 minutes by using a 30 mm-diameter twin-screw extruder having unidirectionally revolving screws (by Ikegai Iron Works) to obtain a polycarbonate resin composition containing the gamma-ray stabilizer.

After that, an injection molding machine (Saicap SG-150U by Sumitomo Juuki Co., Ltd.) and a mold (Spia system by Seiki Co., Ltd.) were used to perform injection molding at a cylinder temperature of 280° C., a manifold temperature of 270° C. and a moving-mold temperature of 70° C. to produce 2-mm thick disk-shaped molded products. The molded products were each subjected to a 25 KGy gamma-ray irradiation treatment in deoxidated atmosphere or in air. A yellowness and yellowing factor were measured within about two days, and the results are shown in Table 3.

TABLE 3

| | (additive) amount | | characteristics of molded product | | yellowing factor ΔYI after 25 KGY γ-ray irradiation | |
|---|---|---|---|---|---|---|
| | benzyl ether compound (A-1) | phosphorous ester compound (B) | Yellow Index (YI) | defects of cloudiness ratio, etc. | in air | in deoxidized gas |
| Example 25 | (a1) 2.5 | (16) 0.08 | 1.5 | 0 | 7.5 | 9.0 |
| Comp. Ex. 12 | (a1) 2.5 | (101) 0.05 | 2.1 | 11 | 8.8. | 16.1 |

In the above table, Comp. Ex. means Comparative Example.

What is claimed is:

1. A gamma-ray stabilizer comprising
   (A) 100 parts by weight of a benzyl compound selected from the group consisting of the following general formulae (1), (2) and (3)

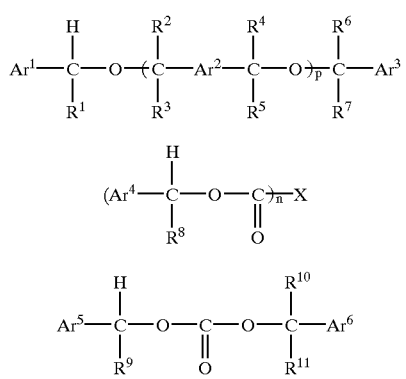

wherein, $R^1$ to $R^{11}$ are each independently selected from the group consisting of a hydrogen atom, alkyl groups having 1 to 5 carbon atoms, cycloalkyl groups having 5 to 6 carbon atoms and aryl groups having 6 to 10 carbon atoms; $Ar^1$, $Ar^3$, $Ar^4$, $Ar^5$ and $Ar^6$ are each independently monovalent aromatic groups having 6 to 20 carbon atoms which can have one or more substituents; $Ar^2$ is a divalent aromatic group having 6 to 20 carbon atoms which can have one or more substituents; p is 0 or 1; X is a direct bond or is an n-valent organic group having 1 to 20 carbon atoms; n is one of the integers 1 through 5; and wherein when n is 1, X is not a direct bond; and wherein the one or more substituents for $Ar^1$, $Ar^2$, $Ar^3$, $Ar^4$, $Ar^5$ and $Ar^6$ are selected from the group consisting of an alkyl group, a cycloalkyl group, an alkoxy group, an acyloxy group, an aralkyl group, an alkoxycarbonyl group, an aromatic group, an acyl group, a cyano group, a nitro group, a carboxyl group, an halogen atom and. an hydroxymethyl group; and
   (B) 0.01 to 10 parts by weight of a pentaerythritol phosphorous ester having a spirocyclic structure.

2. A gamma-ray stabilizer of claim 1 wherein said pentaerythritol phosphorous ester is expressed by the following general formula (4)

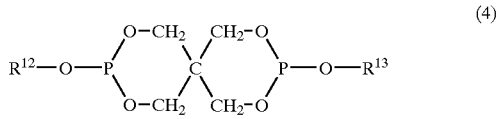

wherein, $R^{12}$ and $R^{13}$ are each independently a hydrogen atom, an alkyl group having 1 to 20 carbon atoms, a cycloalkyl group having 3 to 20 carbon atoms, an aryl group having 6 to 30 carbon atoms, an aralkyl group having more than 6 and up to 30 carbon atoms, an alkylaryl group having more than 6 and up to 30 carbon atoms or a polyhydric phenol residual group.

3. A gamma-ray stabilizer of claim 1 characterized in that said benzyl compound is a benzyl ether compound expressed by formula (1).

4. A gamma-ray stabilizer of claim 1 wherein said benzyl compound is a benzyl ether compound expressed by the following formula (1)-1

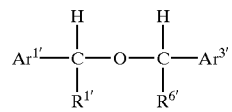

wherein, $R^{1'}$ and $R^{6'}$ are each independently selected from the group consisting of a hydrogen atom, alkyl groups having 1 to 5 carbon atoms, cycloalkyl groups having 5 to 6 carbon atoms and aryl groups having 6 to 10 carbon atoms; $Ar^{1'}$ and $Ar^{3'}$ are each independently a monovalent aromatic group having 6 to 20 carbon atoms.

5. A gamma-ray stabilizer of claim 1 wherein said phosphorous ester is expressed by the following formula (4)-1

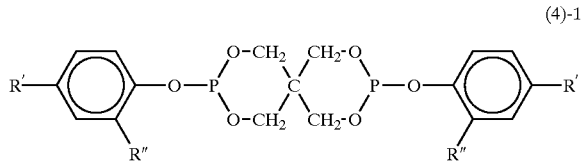

wherein, R' and R" are each independently a tertiary alkyl group having 4 to 20 carbon atoms.

6. A gamma-ray stabilizer of claim 1 wherein said benzyl compound is expressed by formula (1)-1 and said phosphorous ester is expressed by formula (4)-1

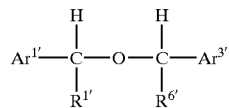
(1)-1 wherein, $R^{1'}$ and $R^{6'}$ are each independently selected from the group consisting of a hydrogen atom, alkyl groups having 1 to 5 carbon atoms, cycloalkyl groups having 5 to 6 carbon atoms and aryl groups having 6 to 10 carbon atoms; $Ar^{1'}$ and $Ar^{3'}$ are each independently a monovalent aromatic group having 6 to 20 carbon atoms, and said phosphorous ester is a compound expressed by the following formula (4)-1

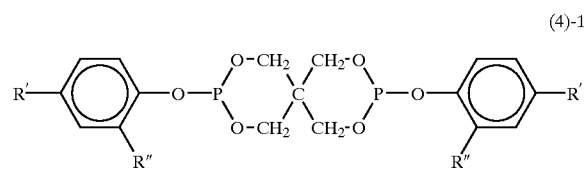
(4)-1 wherein, R' and R" are each independently a tertiary alkyl group having 4 to 20 carbon atoms.

7. A gamma-ray stabilizer of claim 1 wherein said phosphorous ester is expressed by the following formula (4)-2

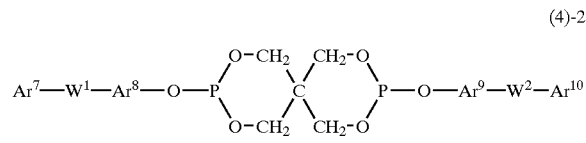
(4)-2 wherein, $Ar^7$ to $A^{10}$ are each independently an aromatic group having 6 to 30 carbon atoms; $W^1$ and $W^2$ are each independently an alkylidene group having 2 to 5 carbon atoms, an alkylene group having 1 to 5 carbon atoms, a cycloalkylidene group having 5 to 6 carbon atoms, a cycloalkylene group having 5 to 6 carbon atoms, a phenyl group-substituted alkylidene group having more than 6 and up to 10 carbon atoms, an oxygen atom, a sulfur atom, a sulfoxide group, a sulfonyl group or a direct bond.

8. A thermoplastic polymer composition which comprises 100 parts by weight of a thermoplastic polymer, 0.01 to 10 parts by weight of a benzyl compound (A) selected from the group consisting of the following general formulae (1), (2) and (3)

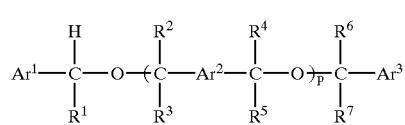
(1)

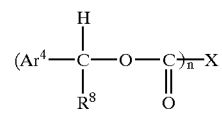
(2)

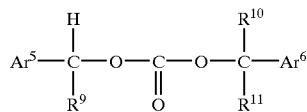
(3)

wherein, $R^1$ to $R^{11}$ are each independently selected from the group consisting of a hydrogen atom, alkyl groups having 1 to 5 carbon atoms, cycloalkyl groups having 5 to 6 carbon atoms and aryl groups having 6 to 10 carbon atoms; $Ar^1$, $Ar^3$, $Ar^4$, $Ar^5$ and $Ar^6$ are each independently a monovalent aromatic group having 6 to 20 carbon atoms which can have one or more substituents; $Ar^2$ is a divalent aromatic group having 6 to 20 carbon atoms which can have one or more substituents; p is 0 or 1; X is a direct bond or an n-valent organic group having 1 to 20 carbon atoms; n is one of the integers of 1 through 5; and wherein where n is 1, X is not a direct bond; and wherein the one or more substituents for $Ar^1$, $Ar^2$, $Ar^3$, $Ar^4$, $Ar^5$ and $Ar^6$ are selected from the group consisting of an alkyl group, a cycloalkyl group, an alkoxy group, and an acyloxy group, an aralkyl group, an alkoxycarbonyl group, an aromatic group, an acyl group, a cyano group, a nitro group, a carboxyl group, an halogen atom and an hydroxymethyl group; and a pentaerythritol phosphorous ester (B) having a spirocyclic structure wherein the phosphorous ester (B) is contained at a ratio of 0.01 to 1 part by weight based on 100 parts by weight of said benzyl compound (A).

9. A thermoplastic polymer composition of claim 8 wherein said thermoplastic polymer is an aromatic polycarbonate mainly composed of a repeating unit expressed by the following formula (5)

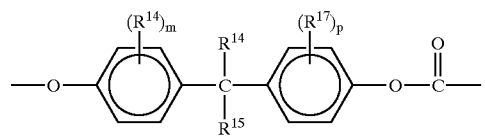
(5)

wherein, $R^{14}$ and $R^{15}$ are each independently selected from the group consisting of a hydrogen atom, alkyl groups having 1 to 5 carbon atoms and cycloalkyl groups having 5 to 10 carbon atoms, and $R^{14}$ and $R^{15}$ can be bonded to each other to form a cycloalkane ring; $R^{16}$ and $R^{17}$ are each independently a substituent selected from the group consisting of alkyl groups having 1 to 5 carbon atoms, halogen atoms and phenyl groups; m and q are each independently 0, 1 or 2.

10. A thermoplastic polymer composition of claim 9 wherein said benzyl compound is a compound expressed by the following formula (1)-1

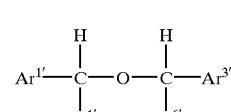
(1)-1 wherein, $R^{1'}$ and $R^{6'}$ are each independently selected from the group consisting of a hydrogen atom, alkyl groups having 1 to 5 carbon atoms, cycloalkyl groups having 5 to 6 carbon atoms and aryl groups having 6 to 10 carbon atoms; $Ar^{1'}$ and $Ar^{3'}$ are each independently a monovalent aromatic group having 6 to 20 carbon atoms, and said phosphorous ester is a compound expressed by the following formula (4)-1

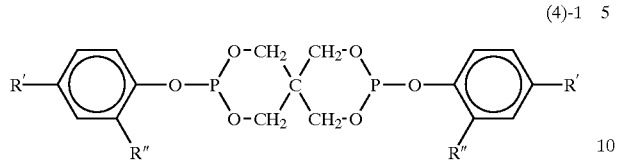

(4)-1 wherein, R' and R" are each independently a tertiary alkyl group having 4 to 20 carbon atoms.

11. An injection molded product made of the thermoplastic polymer composition of claim 9.

12. An injection molded product made of the thermoplastic polymer composition of claim 10.

13. A molded article for medical use made of the thermoplastic polymer composition of claim 9 to be sterilized by gamma-ray irradiation.

14. A molded article for medical use made of the thermoplastic polymer composition of claim 10 to be sterilized by gamma-ray irradiation.

15. An injection molded product of claim 11 wherein the injection molded product is a jacket case for an artificial dialyzer.

16. An injection molded product of claim 12 wherein the injection molded product is a jacket case for an artificial dialyzer.

17. A gamma-ray stabilizer comprising (A) 100 parts by weight of a benzyl compound selected from the group consisting of the following general formulae(1), (2) and (3)

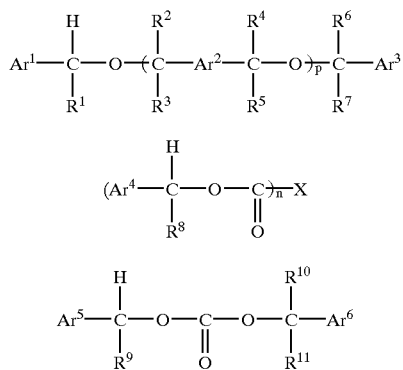

wherein, $R^1$ to $R^{11}$ are each independently selected from the group consisting of a hydrogen atom, alkyl groups having 1 to 5 carbon atoms, cycloalkyl groups having 5 to 6 carbon atoms and aryl groups having 6 to 10 carbon atoms; $Ar^1$, $Ar^3$, $Ar^4$, $Ar^5$ and $Ar^6$ are each independently monovalent aromatic groups having 6 to 20 carbon atoms which can have one or more substituents; $Ar^2$ is a divalent aromatic group having 6 to 20 carbon atoms which can have one or more substituents; p is 0 or 1; X is a direct bond or is selected from the group consisting of an aliphatic residue having 1 to 20 carbon atoms, an alicyclic residue having 6 to 20 carbon atoms and an aromatic residue having 6 to 20 carbon atoms; n is one of the integers 1 through 5; and wherein when n is 1, X is not a direct bond; and wherein the one or more substituents for $Ar^1$, $Ar^2$, $Ar^3$, $Ar^4$, $Ar^5$ and $Ar^6$ are selected from the group consisting of an alkyl group, a cycloalkyl group, an alkoxy group, an acyloxy group, an aralkyl group, an alkoxycarbonyl group, an aromatic group, an acyl group, a cyano group, a nitro group, a carboxyl group, an halogen atom and an hydroxymethyl group; and (B) 0.01 to 10 parts by weight of a pentaerythritol phosphorous ester having a spirocyclic structure.

18. A thermoplastic polymer composition which comprises 100 parts by weight of a thermoplastic polymer, 0.01 to 10 parts by weight of a benzyl compound (A) selected from the group consisting of the following general formulae (1), (2) and (3)

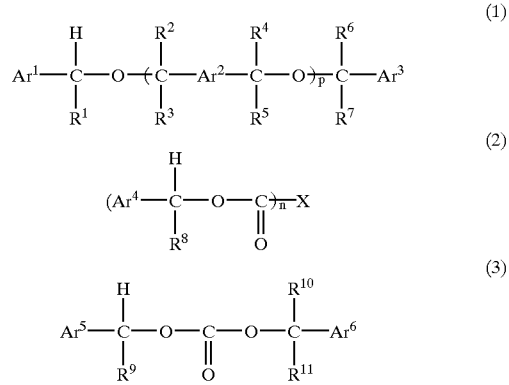

wherein, $R^1$ to $R^{11}$ are each independently selected from the group consisting of a hydrogen atom, alkyl groups having 1 to 5 carbon atoms, cycloalkyl groups having 5 to 6 carbon atoms; $Ar^1$, $Ar^3$, $Ar^4$, $Ar^5$ and $Ar^6$ are each independently a monovalent aromatic group having 6 to 20 carbon atoms which can have one or more substituents; $Ar^2$ is a divalent aromatic group having 6 to 20 carbon atoms which can have one or more substituents; p is 0 or 1; X is a direct bond or is selected from the group consisting of an aliphatic residue leaving 1 to 20 carbon atoms, an alicyclic residue having 6 to 20 carbon atoms and an aromatic residue having 6 to 20 carbon atoms; n is one of the integers of 1 through 6; and wherein when n is 1, X is not a direct bond; and wherein the one or more substituents for $Ar^1$, $Ar^2$, $Ar^3$, $Ar^4$, $Ar^5$ and $Ar^6$ are selected from the group consisting of an alkyl group, a cycloalkyl group, an alkoxy group, an acyloxy group, an aralkyl group, an alkoxycarbonyl group, an aromatic group, an acyl group, a cyano group, a nitro group, a carboxyl group, an halogen atom and an hydroxymethyl group; and a pentaerythritol phosphorous ester (B) having a spirocyclic structure wherein the phosphorous ester (B) is contained at a ratio of 0.01 to 1 part by weight based on 100 parts by weight of said benzyl compound (A).

* * * * *